(12) United States Patent
Ntziachristos et al.

(10) Patent No.: US 8,190,241 B2
(45) Date of Patent: *May 29, 2012

(54) FLUORESCENCE-MEDIATED MOLECULAR TOMOGRAPHY

(75) Inventors: Vasilis Ntziachristos, Larissa (GR); Ralph Weissleder, Peabody, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/126,745

(22) Filed: May 23, 2008

(65) Prior Publication Data

US 2008/0219933 A1 Sep. 11, 2008

Related U.S. Application Data

(63) Continuation of application No. 10/443,463, filed on May 22, 2003, now Pat. No. 7,383,076, which is a continuation of application No. PCT/US01/44764, filed on Nov. 27, 2001, which is a continuation-in-part of application No. 09/723,033, filed on Nov. 27, 2000, now Pat. No. 6,615,063.

(51) Int. Cl.
*A61B 6/00* (2006.01)

(52) U.S. Cl. ........................ 600/473; 600/431

(58) Field of Classification Search ........... 600/476, 600/473, 431

See application file for complete search history.

(56) References Cited

U.S. PATENT DOCUMENTS

| | | | |
|---|---|---|---|
| 4,281,645 A | 8/1981 | Jobsis | 600/324 |
| 4,321,930 A | 3/1982 | Jobsis et al. | 600/344 |
| 4,515,165 A * | 5/1985 | Carroll | 600/475 |
| 4,945,239 A | 7/1990 | Wist et al. | |
| 4,947,850 A | 8/1990 | Vanderkooi et al. | |
| 5,070,455 A | 12/1991 | Singer et al. | |
| 5,090,415 A | 2/1992 | Yamashita et al. | 600/476 |
| 5,136,373 A | 8/1992 | Kamiya et al. | 358/93 |
| 5,186,173 A | 2/1993 | Zuckerman | |
| 5,213,105 A | 5/1993 | Gratton et al. | |
| 5,391,877 A | 2/1995 | Marks | 250/363.03 |
| 5,403,928 A | 4/1995 | Arrhenuis | |
| 5,421,339 A | 6/1995 | Ramanujam et al. | |
| 5,593,658 A | 1/1997 | Bogdanov et al. | |
| 5,641,878 A | 6/1997 | Dandliker et al. | |

(Continued)

FOREIGN PATENT DOCUMENTS

EP 1207385 5/2002

(Continued)

OTHER PUBLICATIONS

Achilefu, S. et al., "Novel receptor-targeted fluorescent contract agents for in vivo tumor imaging," Investigative Biology, 35:479-485 (2000).

(Continued)

*Primary Examiner* — Jacqueline Cheng
(74) *Attorney, Agent, or Firm* — Fish & Richardson P.C.

(57) ABSTRACT

This invention relates to a fluorescence-mediated molecular tomographic imaging system, designed to detect near-infrared fluorescence activation in deep tissues. The system can use targeted fluorescent molecular probes or highly sensitive activatable fluorescence molecular probes. Such probes add molecular specificity and yield high fluorescence contrast, to allow early detection and molecular target assessment of diseased tissue, such as cancers, in vivo. The new tomographic imaging system enables three-dimensional localization in deep tissues and quantitation of molecular probes.

48 Claims, 16 Drawing Sheets

U.S. PATENT DOCUMENTS

| | | | |
|---|---|---|---|
| 5,650,135 A | 7/1997 | Contag et al. | 424/9.1 |
| 5,661,035 A | 8/1997 | Tsien et al. | |
| 5,677,199 A | 10/1997 | Arrhenuis | |
| 5,685,313 A | 11/1997 | Mayevsky | |
| 5,699,798 A | 12/1997 | Hochman et al. | 348/164 |
| 5,762,607 A | 6/1998 | Schotland et al. | |
| 5,827,190 A | 10/1998 | Palcic et al. | |
| 5,846,703 A | 12/1998 | Devlin et al. | |
| 5,865,754 A | 2/1999 | Sevick-Muraca et al. | 600/476 |
| 5,876,946 A | 3/1999 | Burbaum et al. | |
| 5,952,664 A | 9/1999 | Wake et al. | 250/459.1 |
| 6,026,319 A | 2/2000 | Hayashi | 600/476 |
| 6,081,322 A | 6/2000 | Barbour | |
| 6,083,485 A | 7/2000 | Licha et al. | |
| 6,083,486 A | 7/2000 | Weissleder et al. | 424/9.6 |
| 6,108,576 A * | 8/2000 | Alfano et al. | 600/476 |
| 6,205,347 B1 | 3/2001 | Morgan et al. | 600/407 |
| 6,217,847 B1 | 4/2001 | Contag et al. | 424/9.1 |
| 6,224,848 B1 * | 5/2001 | Mills | 424/1.65 |
| 6,258,340 B1 | 7/2001 | Licha et al. | |
| 6,268,222 B1 | 7/2001 | Chandler et al. | |
| 6,274,086 B1 * | 8/2001 | Wilson et al. | 422/82.08 |
| 6,304,771 B1 | 10/2001 | Yodh et al. | 600/476 |
| 6,377,841 B1 | 4/2002 | Lin et al. | 600/477 |
| 6,377,842 B1 | 4/2002 | Pogue et al. | 600/478 |
| 6,397,099 B1 | 5/2002 | Chance | 600/323 |
| 6,526,309 B1 | 2/2003 | Chance | |
| 6,534,041 B1 | 3/2003 | Licha et al. | |
| 6,592,847 B1 | 7/2003 | Weissleder et al. | |
| 6,615,063 B1 | 9/2003 | Ntziachristos et al. | |
| 6,671,540 B1 * | 12/2003 | Hochman | 600/431 |
| 6,825,928 B2 | 11/2004 | Liu et al. | |
| 6,828,966 B1 * | 12/2004 | Gavriliu et al. | 345/420 |
| 7,107,116 B2 * | 9/2006 | Geng | 700/117 |
| 7,383,076 B2 | 6/2008 | Ntziachristos et al. | |
| 7,616,985 B2 * | 11/2009 | Stearns et al. | 600/473 |
| 2003/0170173 A1 * | 9/2003 | Klaveness et al. | 424/1.11 |
| 2005/0149877 A1 | 7/2005 | Rice et al. | |
| 2005/0169843 A1 | 8/2005 | Weissleder et al. | |
| 2005/0283071 A1 | 12/2005 | Ripoll et al. | |
| 2006/0173354 A1 | 8/2006 | Ntziachristos et al. | |
| 2006/0275775 A1 | 12/2006 | Weissleder et al. | |
| 2007/0238957 A1 | 10/2007 | Yared | |
| 2008/0312540 A1 | 12/2008 | Ntziachristos | |

FOREIGN PATENT DOCUMENTS

| | | |
|---|---|---|
| JP | 04 083149 | 3/1992 |
| JP | 04-122248 | 4/1992 |
| JP | 05 223738 A | 8/1993 |
| JP | 08-131445 | 5/1996 |
| JP | 10 206742 | 8/1998 |
| JP | 10508763 A | 9/1998 |
| JP | 11173976 | 7/1999 |
| JP | A-2000-500228 | 1/2000 |
| WO | WO88/04777 | 6/1988 |
| WO | WO97/08538 | 3/1997 |
| WO | WO 98/40106 | 9/1998 |
| WO | WO98/47538 | 10/1998 |
| WO | WO99/20997 | 4/1999 |
| WO | 9940841 A1 | 9/1999 |
| WO | WO99/58161 | 11/1999 |
| WO | 0011024 A2 | 3/2000 |
| WO | 0025113 A1 | 5/2000 |
| WO | WO02/00265 | 1/2002 |
| WO | WO02/41760 | 5/2002 |
| WO | WO02/056670 | 7/2002 |
| WO | WO 03/102558 | 12/2003 |
| WO | WO 2004/072906 | 8/2004 |
| WO | WO 2009/009178 | 1/2009 |
| WO | WO 2009/055095 | 4/2009 |
| WO | WO 2009/120758 | 10/2009 |

OTHER PUBLICATIONS

Ballou, B. et al., "Tumor detection and visualization using cyanine fluorochrome-labeled antibodies," Biotechnology Progress, 13:649-658 (1997).

Bogdanov, Jr. A. et al., "The development of in vivo imaging systems to study gene expression," Trends in Biotechnology, 16:5-10 (1998).

Chance, B., "Near infrared images using continuous, phase-modulated, and pulsed light with quantitation of blood and blood oxygenation," Annals of the NY Acad. Sci., 838:29-45 (1998).

Dellian, M. et al., "Vascular permeability in a human tumour xenograft: molecular charge dependence," British Journal of Cancer, 82:1513-1518 (2000).

Flanagan, Jr. et al., "Functionalized Tricarbocyanine Dyes as Near-Infrared Fluorescent Probes for Biomolecules", Bioconjugate Chem., vol. 8, pp. 751-756 (1997).

Gurfinkel, M. et al., Pharmacokinetics of ICG and HPPH-car for Detection of Normal and Tumor Tissue Using Fluorescence, Near-Infrared Continuous Wave Imaging, MD7-1:245-248.

Kak, A. et al., "Principles of computerized tomographic imaging," IEEE Press, New York, 208-218, (1988).

Mahmood, U. et al., "Near-infrared optical imaging of protease activity for tumor detection," Radiology, 213:866-70 (1999).

Masters B. et al., "Multiphoton Excitation fluorescence microscopy and spectroscopy of in vivo human skin," Biophysical Journal 72:2405-2412 (1997).

Moats, R.A. et al., "A "smart" magnetic resonance imaging agent that reports on specific enzymatic activity," Angewandte Chemie Int. Ed. 36:726-731 (1997).

Ntziachristos, V. et al., "Concurrent MRI and diffuse optical tomography of breast after indocyanine green enhancement," PNAS, 97(6):2767-2772, (2000).

O'Leary, M.A. et al., "Experimental images of heterogeneous turbid media by frequency-domain diffusing-photon tomography," Optical Society of America, pp. 426-428.

Rajadhyaksha, M. et al., "In vivo confocal scanning laser microscopy of human skin: melanin provides strong contrast," J. Invest. Dermatology 104:946-952 (1995).

Tearney et al., "In Vivo Endoscopic Optical Biopsy with Optical Coherence Tomography," Science, 276:2037-2039, (1997).

Tung, C. et al., "In vivo imaging of proteolytic enzyme activity using a novel molecular reporter," Cancer Research 60:4953-4958 (2000).

Tyagi, S. et al., "Molecular beacons: probes that fluoresce upon hybridization," Nat Biotechnology, 14:303-308 (1996).

Tyagi, S. et al., "Multicolor molecular beacons for allele discrimination," Nature Biotechnology 16:49-53 (1998).

Tyagi, S., et al., "Wavelength-shifting molecular beacons," Nature Biotechnology, 18:1191-1196 (2000).

Weissleder, R. et al., "In vivo imaging of tumors with protease-activated near-infrared fluorescent probes," Nat. Biotechnology 17:375-8 (19990.

Weissleder, R. et al., "In vivo magnetic resonance imaging of transgene expression," Nat. Med., 6:351-355 (2000).

Wu, J. et al., "Fluorescence tomographic imaging in turbid media using early-arriving photons and Laplace transforms," Proc. Natl. Acad. Sci. USA, 94:8783-8788, (1997).

Ballou et al., "Tumor Labeling in Vivo Using Cyanine-Conjugated Monoclonal Antibodies," *Cancer Immunol. Immunother* 41:257-263 (1995).

Bogdanov et al., "Long-Circulating Blood Pool Imaging Agents," *Advanced Drug Delivery Reviews* 16:335-348 (1995).

Denmeade et al., "Specific and Efficient Peptide Substrates for Assaying the Proteolytic Activity of Prostate-Specific Antigen," *Cancer Research* 57:4924-4930 (1997).

European Office Action, May 8, 2006.

European Office Action, Mar. 14, 2007.

European Office Action, May 16, 2008.

Folli et al., "Antibody-Indocyanin Conjugates for Immunophotodetection of Human Squamous Cell Carcinoma in Nude Mice," *Cancer Research* 54:2643-2649 (1994).

Folli, S. et al , "Immunophotodiagnosis of colon carcinomas . . . ," Proc. Natl. Adac. Sci. USA, 89:7973-7977 (1992).

Gulnik et al., "Design of Sensitive Fluorogenic Substrates for Human Cathepsin D," *FEBS Letters* 413:379-384 (1997).

International Search Report from PCT/US99/10589, Pub. No. WO 99/58161, mailed Sep. 10, 1999.

International Search Report from PCT/US01/19941, Pub. No. WO 02/00265, mailed Nov. 5, 2001.

International Search Report from PCT/US02/00379, Pub. No. WO 09/056670, mailed Sep. 12, 2002.
International Search Report from PCT/US01/44764, Pub. No. WO 02/041760, mailed Nov. 13, 2002.
Mew, D. et al., "Photoimmunotherapy: Treatment of animal . . . ," Journal of Immunology, 130:1473-1477 (1982).
Neri et al., "Targeting by Affinity-Matured Recombinant Antibody Fragments of an Angiogenesis Associated Fibronectin Isoform," Nature Biotechnology 15:1271-1275 (1997).
Pottier, R.H., et al., "Non-invasive technique for obtaining . . . ," Photochemistry and Photobiology, 44(5):679-687 (1986).
Tromberg et al., "Non-Invasive Measurements of Breast Tissue Optical Properties Using Frequency-Domain Photon Migration," Phil. Trans. R. Soc. London B 352:661-668 (1997).
Tung, Ching-Hsuan. et al., "Preparation of a Cathepsin D Sensitive Near-Infrared Fluorescence Probe for Imaging", *Bioconjugate Chemistry*, vol. 10, pp. 892-896, (1999).
Wagnieres, G. et al., "Photodetection of early cancer in . . . ," SPIE: Future Trends in Biomedical Applications of Lasers, 1525:219-236, (1991).
Weissleder, Ralph, "Molecular Imaging: Exploring the Next Frontier", *Radiology*, vol. 212, pp. 609-614, (1999).
Wouters, Fred S. et al., "Fluorescence Lifetime Imaging of Receptor Tyrosine Kinase Activity in Cells", *Current Biology*, vol. 9, No. 19, pp. 1127-1130, (1999).
Wyatt, "Cerebral Oxygenation and Haemodynamics in the Fetus and Newborn Infant," Phil. Trans. R. Soc. London B 352:697-700 (1997).
Graves et al., "A submillimeter resolution fluorescence molecular imaging system for small animal imaging," Med. Phys. 30(5):901-911, (2003).
Hawrysz and Sevick-Muraca, "Developments Toward Diagnostic Breast Cancer Imaging Using Near-Infrared Optical Measurements and Fluorescent Contrast Agents," Neoplasia, 2(5):388-417, (2000).
Ntziachristos et al, "Multichannel photon counting instrument for spatially resolved near infrared spectroscopy," Review of Scientific Instruments, 70(1):193-201, (1999).
Ntziachristos and Weissleder, "Experimental three-dimensional fluorescence reconstruction of diffuse media by use of a normalized Born approximation," Optics Letters, 26(12):893-895, (2001).
Schotland, "Continuous-wave diffusion imaging," J. Opt. Soc. Am. A, 14(1):275-279, (1997).
International Preliminary Report on Patentability for International Application No. PCT/US01/44764, dated Dec. 21, 2002, 3 pages.
Supplemental Search Report for European Application No. EP 01 98 9794, dated Aug. 18, 2005, 3 pages.
Examination Report for European Application No. EP 01 98 9794, dated Jun. 7, 2006, 4 pages.
Examination and Search Report for European Application No. EP 08 103 270.8, dated Jun. 2, 2009, 6 pages.
Notice of Opposition to European Patent No. EP 1 349 490, filed Oct. 14, 2009, 39 pages.
English Translation of Opposition to European Patent No. EP 1 349 490, filed Oct. 14, 2009, 30 pages.
Aronson, "Boundary conditions for diffusion of light," J. Opt. Soc. Am. A, 12:2532-2539 (1995).
Arridge, "Optical tomography in medical imaging," Topical Review, Inverse Problems 15, R41-R93 (1999).
Benaron et al., "Noninvasive Functional Imaging of Human Brain Using Light," J. Cerebral Blood Flow and Metabolism, 20:469-477 (2000).
Chang et al., "Optical Imaging of Anatomical Maps Derived from Magnetic Resonance Images using Time-Independent Optical Sources," IEEE Transactions on Medical Imaging, 16(1):68-77 (1997).
Li et al., "Diffraction tomography for biochemical imaging with diffuse-photon density waves," Optics Letters, 22:573-575 (1997).
Li et al., "Fluorescent diffuse photon density waves in homogeneous and heterogeneous turbid media: analytic solutions and applications," Applied Optics, 35(19): 3746-3758 (1996).
Li et al., "Near-field diffraction tomography with diffuse photon density waves," Phys. Rev. E., 61(4 Pt B):4295-4309 (2000).
Markel and Schotland, "Inverse problem in optical diffusion tomography. I. Fourier-Laplace inversion formulas," J. Opt. Soc. Am. A Opt. Image Sci. Vis., 18(6):1336-1347 (2001).
Markel and Schotland, "Inverse scattering for the diffusion equation with general boundary conditions," Phys. Rev. E, 64(3 Pt 2):035601:1-4 (2001).
Markel and Schotland, "Symmetries, inversion formulas, and image reconstruction for optical tomography," Phys. Rev. E Stat. Nonlin. Soft Matter Phys., 70(5 Pt 2):056616:1-19 (2004).
Matson et al., "Three-dimensional tumor localization in thick tissue with the use of diffuse photon-density waves," Applied Optics 36:214-220 (1997).
Matson, "Diffraction Tomography for Turbid Media," Advances in Imaging and Electron Physics, 124:253-342 (2002).
Ripoll and Nieto-Vesperinas, "Scattering integral equations for diffusive waves: detection of objects buried in diffusive media in the presence of rough interfaces," J. Opt. Soc. Am. A, 16:1453-1465 (1999).
Ripoll et al., "Spatial resolution of diffuse photon density waves," J. Opt. Soc. Am. A, 16:1466-1476 (1999).
Ripoll et al., "The Kirchhoff Approximation for diffusive waves," Phys. Rev. E, 64:051917:1-8 (2001).
Ripoll and Ntziachristos, "Iterative boundary method for diffuse optical tomography," J. Opt. Soc. Am. A, 20(6):1103-1110 (2003).
Ripoll et al., "Experimental determination of photon propagation in highly absorbing and scattering media," J. Opt. Soc. Am. A, 22(3):546-551 (2005).
Ripoll and Ntziachristos, "From Finite to Infinite Volumes: Removal of Boundaries in Diffuse Wave Imaging", Physical Review Letters, 96:173903:1-4 (2006).
Sevick-Muraca et al., "Fluorescence and Absorption Contrast Mechanisms for Biomedical Optical Imaging Using Frequency-Domain Techniques," Photochem. and Photobio., 66(1):55-64 (1997).
Schotland and Markel, "Inverse scattering with diffusing waves," J. Opt. Soc. Am. A Opt. Image Sci. Vis., 18(11):2767-77 (2001).
European Search Report from corresponding European Application No. 10179910.4, dated Sep. 23, 2011, 6 pages.

\* cited by examiner

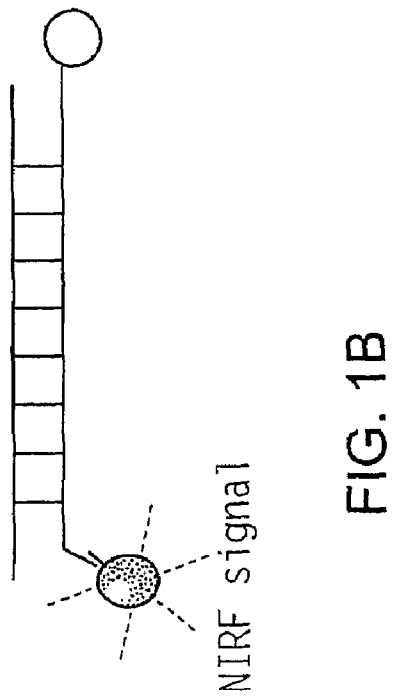
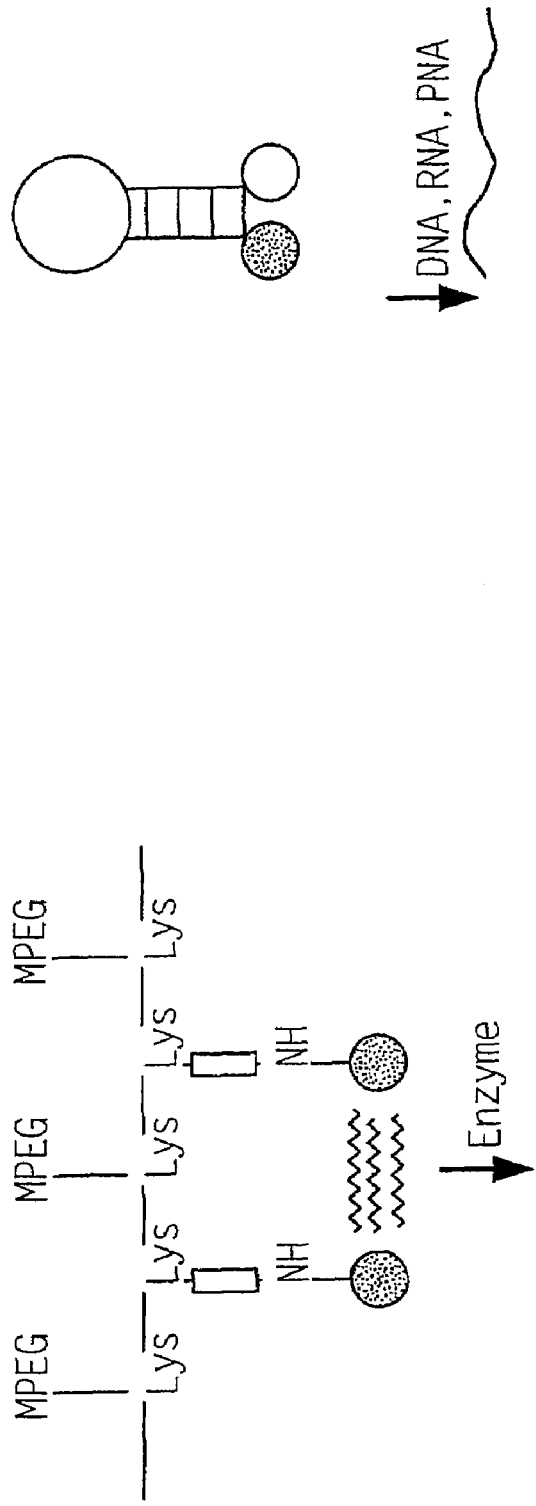
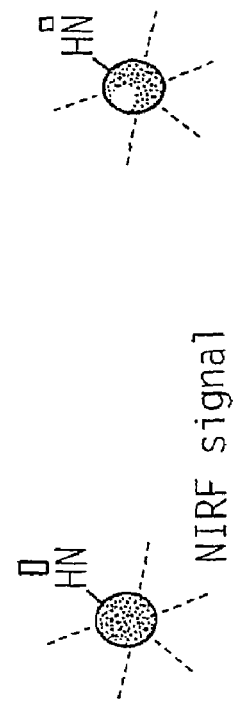
FIG. 1B
FIG. 1A

FIG. 3F
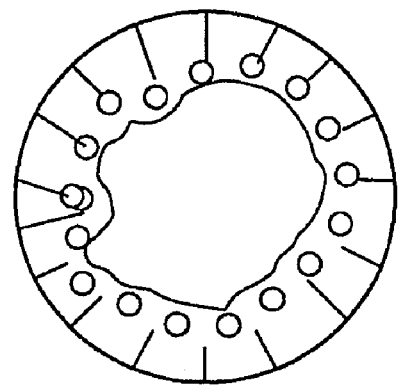
FIG. 3C
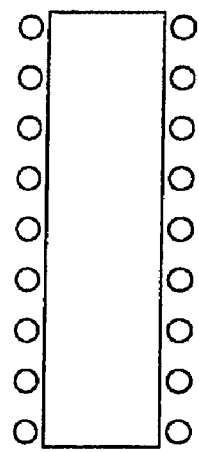
FIG. 3B
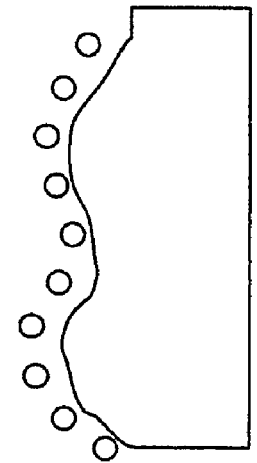
FIG. 3E
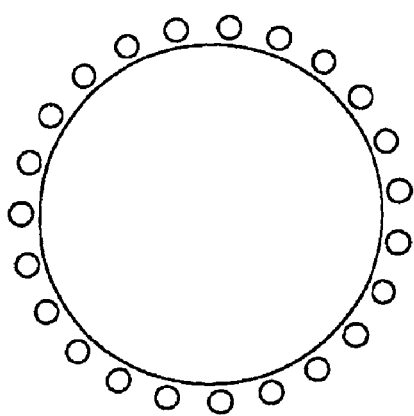
FIG. 3A
FIG. 3D

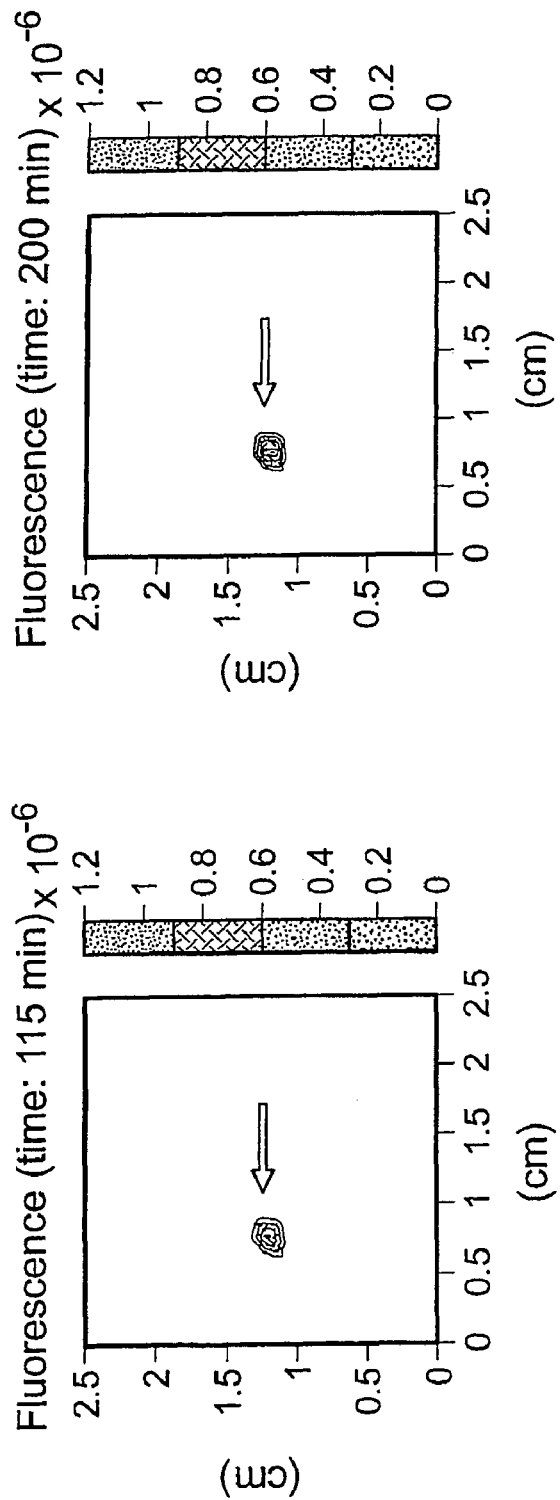
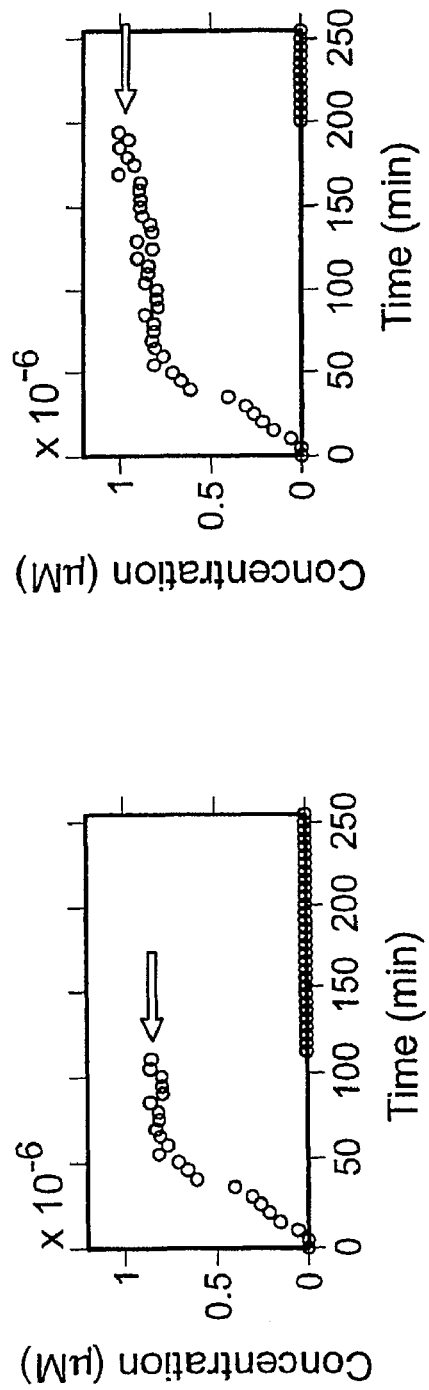
FIG. 8F
FIG. 8E

Kidney Level

Kidney Level

FLUORESCENCE-MEDIATED MOLECULAR TOMOGRAPHY

CLAIM OF PRIORITY

This application is a continuation of U.S. patent application Ser. No. 10/443,463, filed on May 22, 2003, now U.S. Pat. No. 7,383,076, which is a continuation of international application PCT/US01/44764, filed on Nov. 27, 2001, which, in turn, is a continuation-in-part of U.S. patent application Ser. No. 09/723,033, filed on Nov. 27, 2000, now U.S. Pat. No. 6,615,063, the contents of each of which are incorporated herein by reference in their entireties.

TECHNICAL FIELD

This invention relates to extracting quantitative, three-dimensional molecular information from living mammals and patients using fluorochromes and new optical tomographic imaging methods.

BACKGROUND

Molecular imaging can be broadly defined as the characterization and measurement of biological processes at the cellular and molecular level in mammals and human patients. In contradistinction to "classical" diagnostic imaging, for example, magnetic resonance (MR), computed tomography (CT), and ultrasound (US) imaging, molecular imaging analyses molecular abnormalities that are the basis of disease, rather than imaging the end-effects of these molecular alterations. Specific imaging of molecular targets allows earlier detection and characterization of disease, as well as earlier and direct molecular assessment of treatment efficacy. Molecular imaging can theoretically be performed with different imaging technologies, up to now preferably with nuclear imaging technologies, e.g., PET and SPECT imaging) which have high sensitivity of probe detection. The IV administered imaging probes typically recognize a given target. Alternatively, some probes detectable by MR imaging have been developed (Moats et al., Angewandte. Chemie Int. Ed., 36:726-731, 1997; Weissleder et al., Nat. Med., 6:351-5, 2000), although their detection threshold is generally in the micromolar instead of the pico/femptomolar range of isotope probes.

An alternative method is to use fluorescent probes for target recognition. For example, enzyme activatable fluorochrome probes are described in Weissleder et al., U.S. Pat. No. 6,083,486, and fluorescent molecular beacons that become fluorescent after DNA hybridization are described in Tyagi et al., Nat. Biotechnol., 16:49-53, 1998. Fluorescence activatable probes have been used in tissue culture and histologic sections and detected using fluorescence microscopy. When administered in vivo, fluorescence activatable probes have been detected by surface-weighted reflectance imaging (Weissleder et al., Nat. Biotechnol., 17:375-8, 1999); Mahmood et al., Radiology, 213:866-70, 1999. However, imaging in deep tissues (>5 mm from the surface), in absorbing and scattering media such as mammalian tissues, and quantitating fluorescence (and in particular fluorescence activation) has not been described.

To image light interactions in deeper tissues, light in the near infrared (near-IR or NIR) instead of the visible spectrum is preferred. Imaging with near infrared (near-IR or NIR) light has been in the frontier of research for resolving and quantifying tissue function. Light offers unique contrast mechanisms that can be based on absorption, e.g., probing of hemoglobin concentration or blood saturation, and/or fluorescence, e.g., probing for weak auto-fluorescence, or exogenously administered fluorescent probes (Neri et al., Nat. Biotech., 15:1271-1275, 1997; Ballou et al., Cancer Immunol. Immunother., 41:257-63, 1995; and Weissleder, 1999). In either application, NIR photons undergo significant elastic scattering when traveling through tissue. This results in light "diffusion" in tissue that hinders resolution and impairs the ability to produce diagnostically interpretable images using simple "projection" approaches (transillumination), as in x-ray imaging.

During the last decade, mathematical modeling of light propagation in tissue, combined with technological advancements in photon sources and detection techniques has made possible the application of tomographic principles (Kak and Slaney, "Principles of Computerized Tomographic Imaging," IEEE Press, New York, 1988, pp. 208-218); Arridge, Inverse Problems, 15:R41-R93, 1999) for imaging with diffuse light. Diffuse Optical Tomography (DOT) uses multiple projections and deconvolves the scattering effect of tissue. DOT imaging has been used for quantitative, three-dimensional imaging of intrinsic absorption and scattering (see, e.g., Ntziachristos et al., Proc. Natl. Acad. Sci., USA, 97:2767-72, 2000), and also Benaron et al., J. Cerebral Blood Flow Metabol., 20(3):469-77, 2000). These fundamental quantities can be used to derive tissue oxy- and deoxy-hemoglobin concentrations, blood oxygen saturation (Li et al., Appl. Opt., 35:3746-3758, 1996) or hematoma detection in diffuse media.

Although intrinsic-contrast for DOT imaging may be useful in certain situations, e.g., for functional brain activation studies or hematoma detection, these applications do not allow the extraction of highly specific molecular information from living tissues. Fluorochrome concentration has been measured by absorption measurements (Ntziachristos et al., 2000) or by fluorescence measurements in phantoms (Chang et al., IEEE Trans. Med. Imag., 16:68-77, 1997; Sevick-Muraca et al., Photochem. Photobiol., 66:55-64, 1997). However, previously described DOT systems and/or image algorithms have not been useful to obtain three-dimensional quantitation of fluorescence in deep tissues in living mammals.

SUMMARY

The invention is based on the discovery that in vivo fluorochrome signals from specific targeted molecular probes, e.g., probes targeted for specific enzyme activities or DNA sequences, can be localized in three dimensions in deep tissues and be quantitated with high sensitivity using a specially designed imaging system for this purpose and relying on self-calibrated image reconstruction, and new algorithms to extract molecular maps.

In general, the invention features a near-infrared, fluorescence-mediated molecular tomography (FMT) imaging system that includes a NIR light source to provide incident light; a multipoint incident illumination array to direct light into an object, e.g., an animal or human patient, from two or more separate excitation points; multiple optic fibers to transmit light from the light source to each point in the multipoint incident illumination array; a multipoint detection array to collect light, e.g., fluorescent light, emitted from the object from two or more separate collection points; a two-dimensional emitted light array to transmit light emitted from the object to a detector; multiple optic fibers to transmit light from each collection point to a corresponding point on the two-dimensional emitted light array; and a detector to detect and convert light emitted from each point of the two-dimensional emitted light array into a digital signal corresponding to the light emitted from the object.

In this system, the emitted light can be continuous wave (CW) light, time-resolved (TR) light, or both CW and TR light.

The system can further include a processor that processes the digital signal produced 30 by the detector to provide an image on an output device. The output device can provide multiple images simultaneously. The processor can be programmed to process the digital signal by i) generating a corrected fluorescence measurement by subtracting a background signal and filter bleed-through signal from collected fluorescence measurements; ii) generating a corrected intrinsic signal measurement by subtracting a background ambient light signal from collected intrinsic signal measurements; iii) generating a self-calibrated fluorescence measurement by dividing the corrected fluorescence measurement by the corrected intrinsic measurement; iv) generating a corrected background-medium diffuse signal by subtracting the collected background ambient light signal from a collected diffuse signal; and v) generating a self-calibrated intrinsic measurement by dividing the corrected intrinsic signal measurement by the corrected background-medium diffuse signal.

In other embodiments, the processor can be programmed to process the digital signal by i) generating a self-calibrated measurement M=M1−M3/M2−M4, wherein M1 is an emission wavelength fluorescence signal, M2 is an intrinsic signal, M3 is a background bleed-through signal, M4 is a background ambient light signal; ii) generating a self-calibrated intrinsic measurement M'=log (M2−M4)/(M5−M4), wherein M5 is a background-medium diffuse signal; iii) minimizing a function $F(U)=(M-P\times U)2$ to obtain a distribution and magnitude of U, wherein U is a vector of unknown concentration of a target in the object being imaged and P is a forward predictor of M calculated by solving a diffusion equation for an appropriate geometry and background medium in fluorescence mode; iv) minimizing a function $F'(O)=(M'-P'\times O)2$ to obtain a distribution and magnitude of O; wherein O is a vector of unknown concentration of a fluorophore in the object, and P' is a forward predictor of M' calculated by solving a diffusion equation for the appropriate geometry and background medium in absorption/scattering mode; v) calculating an activation ratio AR=U/O; and vi) generating an image corresponding to AR.

The imaging system can include more than 100 optic fibers to transmit light into the patient and/or from each collection point of the detection array, and the detector array can include at least 100 collection points.

In this imaging system, the two-dimensional emitted light array can transmit to the detector a two-dimensional pattern of multiple points of light corresponding to light emitted from the patient in three-dimensions, wherein the pattern varies over time at a rate corresponding to switching of illumination from one to another of the two or more excitation points. In addition, the two or more excitation points are illuminated by the light source one at a time. In certain embodiments the NIR light directed into the object can be at a wavelength of from 550 to 950, e.g., 670 or 750 to 850, nanometers, and the detector can be a charge-coupled device (CCD) camera or include a photomultiplier tube.

The system can also include the NIR fluorescent (NIRF) molecular probes themselves. The probes can be activatable molecular probes.

The invention also features a method for displaying an optical molecular map corresponding to a ratio of a concentration of a molecular probe comprising a fluorophore administered to a patient to a concentration of an activated fluorophore corresponding to a specific target in the patient by: i) providing a first data set of fluorophore concentration based on intrinsic absorption; ii) providing a second data set of activated fluorophore concentration based on fluorescence; iii) dividing the first data set by the second data set on a point-by-point basis to provide a third data set; and iv) processing the third data set to provide an optical molecular map corresponding to a ratio of a concentration of a molecular probe comprising a fluorophore to a concentration of an activated fluorophore corresponding to a specific target in the patient.

In another aspect, the invention features a method of obtaining a three-dimensional, quantitative, molecular tomographic image of a target region within a patient, by administering a near-infrared fluorescent (NIRF) molecular probe to the patient, wherein the molecular probe selectively accumulates within a target region in the patient; directing near-infrared light from multiple points into the patient; detecting fluorescent light emitted from the patient; and processing the detected light to provide a three-dimensional image that corresponds to the three-dimensional target region within the patient and to the quantity of molecular probe accumulated in the target region.

In this method, the three-dimensional image can be visualized on a two-dimensional output device. The processing can include digitizing the fluorescent signal emitted from the patient, self-calibrating the digital signal by combining fluorescent and intrinsic signal measurements from the patient and background medium, and reconstructing a three-dimensional, quantitative image. In certain embodiments, the processing includes i) generating a corrected fluorescence measurement by subtracting a background signal and filter bleed-through signal from collected fluorescence measurements; ii) generating a corrected intrinsic signal measurement by subtracting a background ambient light signal from collected intrinsic signal measurements; iii) generating a self-calibrated fluorescence measurement by dividing the corrected fluorescence measurement by the corrected intrinsic measurement; iv) generating a corrected background-medium diffuse signal by subtracting the collected background ambient light signal from a collected diffuse signal; and v) generating a self-calibrated intrinsic measurement by dividing the corrected intrinsic signal measurement by the corrected background-medium diffuse signal.

The processing can also include i) generating a self-calibrated measurement M=M1−M3/M2−M4, wherein M1 is an emission wavelength fluorescence signal, M2 is an intrinsic signal, M3 is a background bleed-through signal, M4 is a background ambient light signal; ii) generating a self-calibrated measurement M'=log (M2−M4)/(M5−M4), wherein M5 is a background-medium diffuse signal; iii) minimizing a function $F(U)=(M-P\times U)2$ to obtain a distribution and magnitude of U, wherein U is a vector of unknown concentration of a target in the object being imaged and P is a forward predictor of M calculated by solving a diffusion equation for an appropriate geometry and background medium in fluorescence mode; iv) minimizing a function $F'(O)=(M'-P'\times O)2$ to obtain a distribution and magnitude of O; wherein O is a vector of unknown concentration of a fluorophore in the object, and P' is a forward predictor of M' calculated by solving a diffusion equation for the appropriate geometry and background medium in absorption/scattering mode; v) calculating an activation ratio AR=U/O; and vi) generating an image corresponding to AR.

In these methods, the molecular probes can be administered systemically or locally by injecting a molecular probe, e.g., an activatable probe. The molecular probe can be locally injected into the target region or into a non-target region, for example, by intraperitoneal administration with systemic absorption and administration by an implanted slow-release compound or device such as a pump.

In certain embodiments of the new methods, the NIR light can be directed into the patient from at least 32 separate points of light arranged in a fixed three-dimensional geometry, or with a multipoint incident illumination array comprising a belt having at least 12 points of light. In addition, the spatial localizations of the multipoint incident illumination array and the multipoint detector array can be determined by image co-registration. In other embodiments, photon pulses are directed into the patient and the arrival of photons emitted from the patient is time-resolved using a separate array of photon detectors.

The emitted fluorescent light in these methods can be continuous wave (CW) light, time-resolved (TR) light, or both CW and TR light. In addition, the methods can be performed dynamically as function of time, and the image can be co-registered with an image obtained by magnetic resonance or computed tomography imaging. The multipoint incident illumination array (or detector array) can include a fiducial, and wherein the fiducial is used to determine the spatial localization of the array on the object.

The invention also features a method of detecting a cellular abnormality in a patient by using molecular probes targeted to a particular cellular abnormality, e.g., associated with a disease such as cancer, a cardiovascular disease, AIDS, a neurodegenerative disease, an inflammatory disease, or an immunologic disease. The invention also features a method of assessing the effect of a compound on a specified molecular target by using a molecular probe that is activated by the molecular target, wherein the probe is contacted to the target, the target is imaged prior to and after contact with the molecular probe, and the corresponding images are compared, wherein a change in the molecular target indicates the compound is effective. For example, the specified molecular target can be a protease, and the compound can be a protease inhibitor.

A molecular probe is a probe that is targeted to a molecular structure, such as a cell-surface receptor or antigen, an enzyme within a cell, or a specific nucleic acid, e.g., DNA, to which the probe hybridizes. A fluorophore is an agent that fluoresces. A fluorochrome is an agent that fluoresces (e.g., a fluorophore) and has a color.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

The new methods and systems provide various advantages. For example, the new methods and systems provide for the first time the ability to detect fluorescence activation, e.g., by enzyme activation, in deep tissue and to provide localization and quantitation in three dimensions. In addition, the new methods provide non-invasive, molecular imaging to provide information at subcellular levels.

The impact of the new molecular imaging techniques is potentially enormous. First, the new methods and systems can provide insight into specific molecular abnormalities that form the basis of many diseases, e.g. up-regulated proteases, other enzymes, cell surface receptors, cyclins, cytokines or growth factors in cancer. Second, the new methods can be used to assess efficacy of novel targeted therapies at a molecular level, long before phenotypic changes occur. This, in turn, is expected to have an impact in drug development, drug testing, and choosing appropriate therapies and therapy changes in a given patient. Third, the new molecular imaging/quantitation methods and systems potentially enable one to study the genesis of diseases in the intact microenvironment of living systems. Fourth, the new methods of fluorescence-mediated molecular tomographic imaging are useful for testing novel drug delivery strategies. Fifth, the imaging methods allow one to gain three-dimensional information that is much faster to obtain than is currently possible with time consuming and labor intensive conventional, basic science techniques.

The new imaging systems and methods will have broad applications in a wide variety of novel biologic, immunologic, and molecular therapies designed to promote the control and eradication of numerous different diseases including cancer, cardiovascular, neurodegenerative, inflammatory, infectious, and other diseases. Furthermore, the described detection systems and methods will have broad applications for seamless disease detection and treatment in combined settings.

Other features and advantages of the invention will be apparent from the following detailed description, and from the claims.

DESCRIPTION OF THE DRAWINGS

FIGS. 1A and 1B are examples of auto-quenched, activatable, near-infrared (NIR) fluorescent probes particularly suited for use in the new methods.

FIGS. 3A to 3F are a series of schematic diagrams of alternative embodiments of multipoint incident light arrays including circular arrays (as also shown in FIG. 2A), planar arrays, curved arrays, molded arrays, belt arrays, and catheter arrays. All of these embodiments can be used with the system shown in FIG. 2A.

FIG. 7A shows the phantom setup, and FIG. 7B illustrates the reconstructed image.

FIGS. 8C-8F are still images of a time-lapse video made of the enzyme activity observed in the experimental setup shown in FIG. 8A at 20 (8C), 50 (8D), 115(8E), and 200 (8F) minutes, respectively.

FIG. 9A is a T2-weighted MR image. FIG. 9B is a NIR fluorescence-mediated molecular tomography (FMT) image of the tumor obtained 24 hours after intravenous injection of an activatable cathepsin B-reporting NIR imaging probe. FIG. 9C is a fused image that demonstrates the good co-registration of the tumor as it is seen on the T2-weighted MR image and on the NIRF-activated FMT image.

Like reference symbols in the various drawings indicate like elements.

DETAILED DESCRIPTION

Figure 2B:
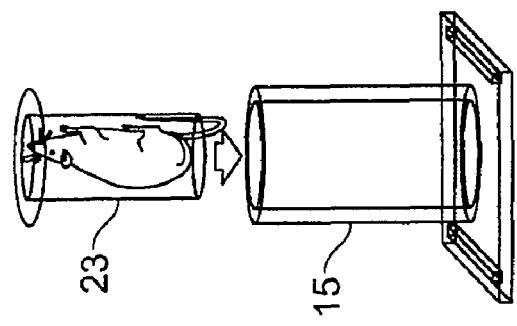
FIG. 2B is a schematic diagram of a positioning device used in conjunction with the apparatus of FIG. 2A to hold an animal in proper position for imaging.

This invention relates to extracting quantitative molecular information from living mammals and patients using fluorochromes, e.g., activatable fluorochromes, and a novel optical tomographic imaging method. This fluorescence-mediated molecular tomographic (FMT) imaging system is specifically designed to detect NIR fluorescence (NIRF) activation in deep tissues with high sensitivity, quantitatively and over time. The system can use activatable NIRF molecular probes that are quenched and do not fluoresce until activated or highly sensitive targeted NIRF molecular probes. The activatable molecular fluorochrome probes add molecular specificity and yield high fluorescence contrast, to allow early detection and molecular target assessment of cancers and other diseased tissue in vivo. The systems include various components for obtaining the image data and one or more processors that include new algorithms to process the data to provide the high levels of information and resolution.

The FMT imaging methods and systems enable extraction of molecular information from diseased tissue. Thus, the systems and methods can be used to detect many molecular aberrations, as they occur in cancer, cardiovascular disease, inflammation, immunological diseases, arthritis, cutaneous and ophthalmic diseases, and others.

After reviewing the suitable probes and the general methodology of optical imaging, we will describe the new imaging systems and the processing required to obtain useful three-dimensional, quantitative information.

Activatable NIR Fluorescent Probes

A fundamental paradigm shift in injectable contrast agents has recently been introduced by synthesizing probes that are become brightly fluorescent following conversion by specific enzymes (Weissleder et al., Nat. Biotechnol., 17:375-378, 1999) or become fluorescent by DNA hybridization (Tyagi et al., Nat. Biotechnol., 14:303-308, 1996). In their native state the probes are quenched either by a small molecule quencher (e.g., DABCYL (a non-fluorescent chromophore that serves as a universal quencher for any fluorophore in a molecular beacon: 4-(4-dimethylaminophenylazo)-benzoic acid) or QSY-7) or by multiple fluorochromes (e.g., through energy resonance transfer. FIGS. 1A and 1B show schematics of two probes designed to target a specific enzyme (1A) and a specific DNA sequence (1B). When the fluorochrome is released or spatially separated from its quencher, fluorescence can increase up to 1000 fold. Because the spatial rearrangement of the quenched fluorochromes occurs only after specific interactions, these probes can be used to extract molecular information from living organism. These activatable probes have four major advantages over other methods when single fluorochromes are attached to affinity molecules: (1) a single enzyme can cleave multiple fluorochromes, thus resulting in one form of signal amplification, (2) reduction of background "noise" by several orders of magnitude is possible, (3) very specific enzyme activities can potentially be interrogated, and (4) multiple probes can be arranged on delivery systems to simultaneously probe for a spectrum of enzymes.

A panel of highly specific enzyme sensitive molecular probes have been synthesized that target matrix metalloproteinase-2 (MMP-2), cathepsin B/H, cathepsin D, cathepsin K, PSA, and caspase-3), and which are capable of fluorescence activation at 600-900 nm. These probes are described in detail in Weissleder et al., U.S. Pat. No. 6,083,486; Weissleder et al., Nat. Biotechnol., 17:375 (1999); Tung et al., Cancer Research, 60:4953-8, 2000; and Tung et al., Bioconj. Chem., 10:892-896, 1999). The activatable sensitive probes typically consist of three building blocks: (1) fluorochromes, (2) target substrate, and (3) a delivery vehicle.

Reporter fluorochromes: Hundreds of optical probes have been developed for microscopy and photodynamic therapy. Of these, fluorescent probes (i.e., excitation at shorter wavelength and emission at longer wavelength) are ideally suited for studying biological phenomena, as has been done extensively in fluorescence microscopy. If fluorescent probes are to be used in living systems, the choice is generally limited to the near infrared spectrum (600-1000 nm) to maximize tissue penetration by minimizing absorption by physiologically abundant absorbers such as hemoglobin (<550 nm) or water (>1200 nm). Ideally the fluorochromes are designed to emit at 800±50 nm. A variety of NIRF molecules have been described and/or are commercially available, including: Cy5.5 (Amersham, Arlington Heights, Ill.); NIR-1 (Dojindo, Kumamoto, Japan); IRD382 (LI-COR, Lincoln, Nebr.); La Jolla Blue (Diatron, Miami, Fla.); ICG (Akorn, Lincolnshire, Ill.); and ICG derivatives (Serb Labs, Paris, France). NIRF probes for in vivo use ideally should have the following properties: (1) narrow emission bandwidths, (2) high fluorescence efficiency (quantum yield), (3) biocompatibility, and (4) spectrally separated absorption and excitation.

Target Substrates: The release and or availability of individual fluorochromes is determined by interaction of a target substrate with its target. A target substrate can, for example, be a peptide sequence that is cleaved by enzymes (see Table 1 below), a phosphate group which is transferred by certain kinases, or a hybridizing DNA sequence recognizing a specific complementary DNA motif (see FIG. 1B).

TABLE 1

Examples of Peptide Substrates (dots indicate the cleavage site)

| Protease target | Peptide sequence |
| --- | --- |
| Cathepsin D | GPIC(Et)F•FRLG |
| Cathepsin B | GRR•G |
| Matrix metalloproteinase 2 | GPLG•VRG |
| Caspase 3 | DEVD•G |
| Prostate specific antigen | HSSKLQ•G |

Delivery Vehicle: For a quenched probe to reach its intended target, it has to evade rapid clearance/elimination and overcome several structural barriers to delivery. These barriers include: (1) extravasation from vessels, (2) diffusion through tissue, and (3) cell membrane translocation in the case of intracellular enzymes (not required for secreted enzymes). These barriers to delivery are fairly well investigated, and delivery vehicles can be selected using standard techniques and information. Suitable vehicles to deliver fluorochromes and substrates to a target, e.g., a tumor, in the body can be selected from a group of polymers, including protected graft co-polymers (Marecos et al., Bioconjug. Chem., 9:184-191, 1998) containing polyethylene glycol (PEG), polaxamers, and/or carbohydrates. Additional delivery vehicles include dendrimers, proteins, carbohydrates, lipid spheres (e.g., emulsions, liposomes, and lipid self-assemblies), nanoparticles, and other materials commonly used for parenteral drug delivery.

Specific probes based on the above design for use in the new methods can be prepared as described in detail in Weissleder et al., U.S. Pat. No. 6,083,486; Weissleder et al., Nat. Biotechnol., 17:375-8, 1999; and Tung et al., Bioconj. Chem., 10:892-896, 1999.

One specific example of enzyme activatable probes for use in the new methods can be prepared as follows (see, Weissleder et al., U.S. Pat. No. 6,083,486; Weissleder et al., Nat. Biotechnol., 17:375-8, 1999). A protected graft copolymer (PGC) consisting of a poly-L-lysine (PL) backbone and methoxy poly-e-ethylene glycol (MPEG) side chains is first synthesized (Bogdanov et al., J. Drug Targeting, 4:321-330, 1997). In one example, Cy5.5 (absorption=675 nm, emission=694 nm, Amersham, Arlington Heights, Ill.) can be directly attached to the poly-lysine backbone, yielding an activatable probe that can be cleaved by cathepsin B/H and trypsin and has been used for the experiments described below. Briefly, an excess of monoactivated Cy5.5 was reacted with PGC at pH 8.0 to yield the probe. The final products were separated from free dye by size-exclusion chromatography. Trypsin and cathepsin B/H-like proteases are capable of cleaving such probes as occasional free lysine residues represent an enzyme substrate.

Alternatively, one can attach specific peptides conferring enzyme specificity directly to the PGC graft copolymer. For example, cathepsin D sensitive probes have been synthesized (Tung et al., Cancer Res., 60: 4953-8, 2000 and Tung et al., Bioconj. Chem., 10:892-896, 1999). Briefly, PGC was reacted with large excess of iodoacetyl anhydride to convert all amino groups on the polylysine backbone into iodol groups. The cathepsin D specific peptide, GIC(Et)FFKK (Fitc)C was attached to the iodinated PGC through a thiol specific reaction. Thereafter, Cy5.5 was attached to the N-terminus and the free lysine side chains of the cathepsin D substrate peptide. The advantage of this design is twofold: (1) a high loading capacity (due to the fact that all lysines can be modified), and (2) that the fluorochrome spacer is readily accessible to enzymes, thus resulting in improved release kinetics and signal recovery.

Other NIR Fluorescent Probes The probes described above are specifically designed to become activated upon target interaction, e.g., target enzyme interaction. Alternative probes that can be used in the new detection methods include (1) probes that become deactivated (quenched) after target interaction, (2) probes that change their quantum yield upon target interaction, (3) probes that change their fluorescence lifetime after target interaction, (4) probes that change their fluorescence spectrum after target interaction, (5) wavelength shifting beacons (Tyagi et al., Nat. Biotechnol., 18:1191-1196, 2000), (6) multicolor fluorescence probes (Tyagi et al., Nat. Biotechnol., 16:49-53, 1998), or (7) probes that have high binding affinity to targets, i.e., that remain within a target region while non-specific probes are cleared from the body. Examples of the latter probes include receptor-targeted NIR fluorochromes (Achilefu et al., Invest. Radiol., 35:479-485, 2000) or antibody-targeted NIR fluorochromes (Ballou et al., Biotechnol. Prog., 13:649-658, 1997. Another group of suitable fluorescent probes are long lifetime lanthanide metal-ligand probes that will allow the use of gated detection, and further increased sensitivity.

General Methodology

The new systems use a charge-coupled device (CCD) camera and lens system to obtain "tomographic measurements" from the periphery of a multipoint incident light array, such as a cylinder with numerous, spaced, light emitters, for three-dimensional optical scans. Improvements in NIR image quality are related to the number of sources and detectors used. The advantage of CCD technology is that increasing the detector density does not require additions in the detection hardware, just additional optic fibers to create a bigger array.

Fluorescence-Mediated Molecular Tomography (FMT)

The tomographic methodology described herein is an improvement of the general category of tomography using diffracting sources (see, e.g., Kak and Slaney, "Principles of Computerized Tomographic Imaging," IEEE Press, New York, 1988, pp. 208-218). The technique uses measurements of light at multiple projections to obtain information of the optical contrast inside turbid media such as tissue. In brief, diffraction tomography segments the volume under investigation into a number of discrete voxels, referred to as a "mesh." The analysis is divided into two steps. The first step is the "forward problem," in which a diffusion equation is used to describe the photon propagation into an assumed medium, e.g., tissue, and is used to predict the field detected from this medium. The second step is the "inverse problem," in which the optical properties of each voxel of the assumed medium are updated to minimize the errors observed between the predicted and measured fields. There are several ways to calculate the forward problem (analytical and numerical solutions of the diffusion equation) and inverse problem (direct inversion, $\chi^2$-based fits, and algebraic reconstruction techniques). Here we use a numerical solution of the forward problem to generate the prediction vectors for the fluorescence and intrinsic signal measurements (See also FIG. 5). Inversion is based on the relaxed algebraic reconstruction technique. Higher order solutions can be obtained if needed when a solution is fed back in the forward problem to produce more accurate forward propagation models, and this process can be repeated iteratively.

The new FMT imaging systems use one or more laser sources to detect specific chromophores or fluorophores and the forward problem is calculated for the specific wavelength (s) used. Laser diodes are used as light sources since they produce adequate power, are within the FDA class I and class II limits, and are stable, wavelength-specific and economical. Light is directed to and from tissue using fiber guides, as this allows flexibility in the geometrical set-up used. For optical coupling the fibers have to be in contact with tissue. Alternatively, matching fluid is used to eliminate reflections due to air-silica-tissue index of refraction mismatch.

Three different light source-detection technologies exist. Any combination of them can be used for FMT applications as described herein. The simplest is continuous wave (CW) imaging. This technique uses light of constant intensity and measures either (1) the signal due to a distribution of excited fluorophores or (2) the attenuation of light (due to tissue absorption and scattering) employing multiple source-detector pairs. The technique is technically relatively simple and usually offers the best signal-to-noise (SNR) characteristics. However, it is not best suited for imaging of intrinsic tissue contrast since it usually introduces significant cross-talk between the calculations and imaging of absorption and scattering coefficients. On the other hand, if the background optical properties are known, the method is well-suited for imaging fluorophore concentration in the steady-state. To produce activation information, a combination of this technologically simple approach with a technology richer in information content can be used to obtain a both fluorescence and intrinsic contrast images. A specific design is described below, in which the light source is switched from one light emitter to another on a multipoint array in series, so that only one emitter is illuminated at a time.

A more elaborate approach is to use intensity modulated (IM) light at a single or at multiple frequencies. With this method, modulated light attenuation and phase shifts, relative to the incident light, can be measured for multiple source-detector pairs. Compared to a CW measurement, which yields intensity attenuation, the IM technique offers two pieces of information, i.e., intensity attenuation and phase shift per source-detector pair. Amplitude and phase are usually uncorrelated measurements and can more efficiently resolve the absorption and scattering coefficient of intrinsic contrast. In the fluorescence mode, the technique can image two sets of information, fluorophore concentration and fluorescence lifetime.

The third approach, the time-resolved (TR) technique, uses short pulses of light injected into the tissue. The technique resolves the distribution of times that the detected photons travel into the medium for multiple source-detector pairs. Time-resolved methods contain the highest information content per source-detector pair, comparable only to the IM method performed simultaneously at multiple frequencies. This can be easily explained when one considers that the Fourier transform of the time-resolved data yields information at multiple frequencies up to 1 GHz, including the continuous wave components (f=0 MHz) used by the previous two methods. Therefore, the time-resolved method offers a CW component for direct comparison with the CW system, but also intensity attenuation and phase-shift measurements at multiple-frequencies (via the Fourier transform) that can image intrinsic absorption and scattering, and also fluorophore concentration and fluorescence lifetime.

A cost-efficient embodiment of the invention is described in detail below (see FIGS. 2A-2C and FIG. 4). In this embodiment, the bulk information is collected using economical, massively parallel CW measurements (~1000 channels) and highly specific information of absorption and scattering parameters are collected with a smaller array of time-domain source-detection channels (~50-100 channels). The time-domain information is used in three ways. The first is to independently quantify the average absorption and reduced scattering coefficient at the emission and excitation wavelength. The second is to implement time-domain measurements of intrinsic signal into the intrinsic reconstruction scheme by Fourier transforming the time-domain data, hence obtaining multiple-frequency readings. Since the tomographic problem is written in the frequency domain (with CW measurements having zero frequency) the addition of extra, higher frequency measurements is straightforward (just adding additional lines in the weight matrix constructed for the appropriate frequency, for both real and imaginary decompositions). The third use of the time domain system is to implement time-domain measurements of fluorescent signal into the fluorescent reconstruction scheme by Fourier transforming the time-domain data, and obtain information of the fluorescence lifetime of the NIRF probe.

Fluorescence-Mediated Molecular Tomographic (FMT) Imaging Systems

The new imaging systems include an apparatus with various components used to generate digital signal data from analog fluorescence emitted from a patient or animal body, and a processor programmed with algorithms that can process the digital signal data into useful images that provide diagnostic and prognostic information. The systems can also obtain measurements of the incident light after it propagates through the tissue and obtain information on the intrinsic contrast of the body being imaged.

Apparatus

Diffraction tomography differs from simple projection imaging in that it requires tissue transillumination at multiple projections. Therefore the construction of an appropriate light guiding apparatus is fundamental to obtain molecular tomographic images using NIR light. In one embodiment, the system features a multipoint incident illumination array and a multipoint detector array, both incorporated into a single cylinder, to be placed around the animal or patient body. One such apparatus is shown in FIG. 2A and FIG. 4. The two instruments can operate sequentially.

System 10 includes a continuous wave (CW) laser source 12. The laser 12 uses constant intensity light. Two wavelengths obtained from two different lasers can be used for imaging the intrinsic contrast before the administration of the NIRF probe. For imaging the fluorochrome Cy 5.5, one wavelength is set to 673 nm (excitation wavelength) and the other to 694 nm (emission wavelength). Imaging at both wavelengths is necessary so that accurate forward models are created for the excitation field from the source to the fluorophore and for the emission field from the fluorophore to the detector. The other combination of wavelengths will target the fluorochrome ICG at 750 nm (excitation) and 800 nm (emission). The two wavelengths are time-shared since the measurements are not very demanding in terms of time efficiency and are coupled through an optical attenuator 14 to a 1×32 optical switch 16 (e.g., an optical switch from Dicon FiberOptics Irvine Calif.). The optical switch 16 directs light from laser 12 to any one of multiple (sixteen in this embodiment) source fibers 18. Alternatively, all fibers can be illuminated simultaneously, each at a different wavelength. The key is to be able to distinguish each point of illumination on the multipoint incident illumination array 20.

In this embodiment, the multipoint incident illumination array 20 is located within a resin cylinder 15 (also referred to herein as an "imaging chamber"), with several rings of multiple source fibers 18 connected around the cylinder. In essence, cylinder 15 has numerous holes drilled into it in a series of "rings" at different levels of the cylinder and perpendicular to the central axis. The holes can be equally spaced around the perimeter of the cylinder. The source fibers 18 pass through the holes in cylinder 15 and end flush with the inner wall. A multipoint detector array 21 is incorporated into the same cylinder 15, in the form of rings of detector fibers 22 interleaved (alternating) with the rings of the source fibers 18. Again, the cylinder has holes drilled for each detector fiber. This provides three-dimensional volume coverage within the cylinder. Detector fibers 22 form the detector array 21 of cylinder 15, and, like the source fibers, end flush with the inner wall of the cylinder. In this first implementation, three rings of twelve detection fibers each are interleaved with two rings of sixteen source fibers each, each ring at 3 mm from the next, thus covering a total cylinder height of 1.2 cm.

Cylinder 15 (including multipoint incident illumination array 20 and multipoint detector array 21) can be filled with a liquid optical contact medium (e.g., Intralipid® or an emulsion of $TiO_2$ particles and appropriate amounts of an absorbing fluorophore or fluorochrome that simulate the optical properties of the tissue examined), which serves as the "coupling" fluid of diffuse photons from the surface of the animal body to the detection fibers. The concentration of $TiO_2$ particles for the matching fluid and the resin cylinder will be such as to induce scattering properties comparable with the average reduced scattering coefficient of mice.

Fluorescent light collected by multipoint detector array 21 is fed through detector fibers 22 to a two-dimensional emitted fluorescent light array 24. The two-dimensional array 21 transmits the analog fluorescent light emitted from the body through a long-pass filter 25 (depending on the fluorochrome used) and to a CCD camera 26. The long-pass filter 25 will be selected for the appropriate cut-off wavelength, similar as done for surface reflectance type on imaging systems (Mahmood, Radiology, 213:866-870, 1999). To image intrinsic contrast the filter is removed. The CCD camera 26 is mounted on a breadboard, and a lens 27, or a system of macro lenses, images the two-dimensional emitted fluorescent light array onto the CCD camera.

Optimum light attenuation will be set by the optical attenuator 14 so that measurements will not saturate the CCD camera. For a typical 16-bit CCD camera the useful dynamic range is approximately three to four orders of magnitude. This is also the dynamic range expected for measurements of diffuse light in small animals with body diameters of about 2-3 cm. The dynamic range expected for human patients may differ depending on the target organ. For example, for human breast imaging, at an approximate diameter of 8 cm, the dynamic range required is about 6-8 orders of magnitude. This dynamic range can be covered using CCD technology by rapidly acquiring multiple frames. With current CCD technology used at 10 frames per second, the dynamic range can be 6 orders of magnitude in one second of acquisition. For brain measurements, higher dynamic range may be achieved with longer acquisition times or more time-efficiency by using programmable attenuators that selectively attenuate the higher signals with a known level of attenuation.

Figure 2A:
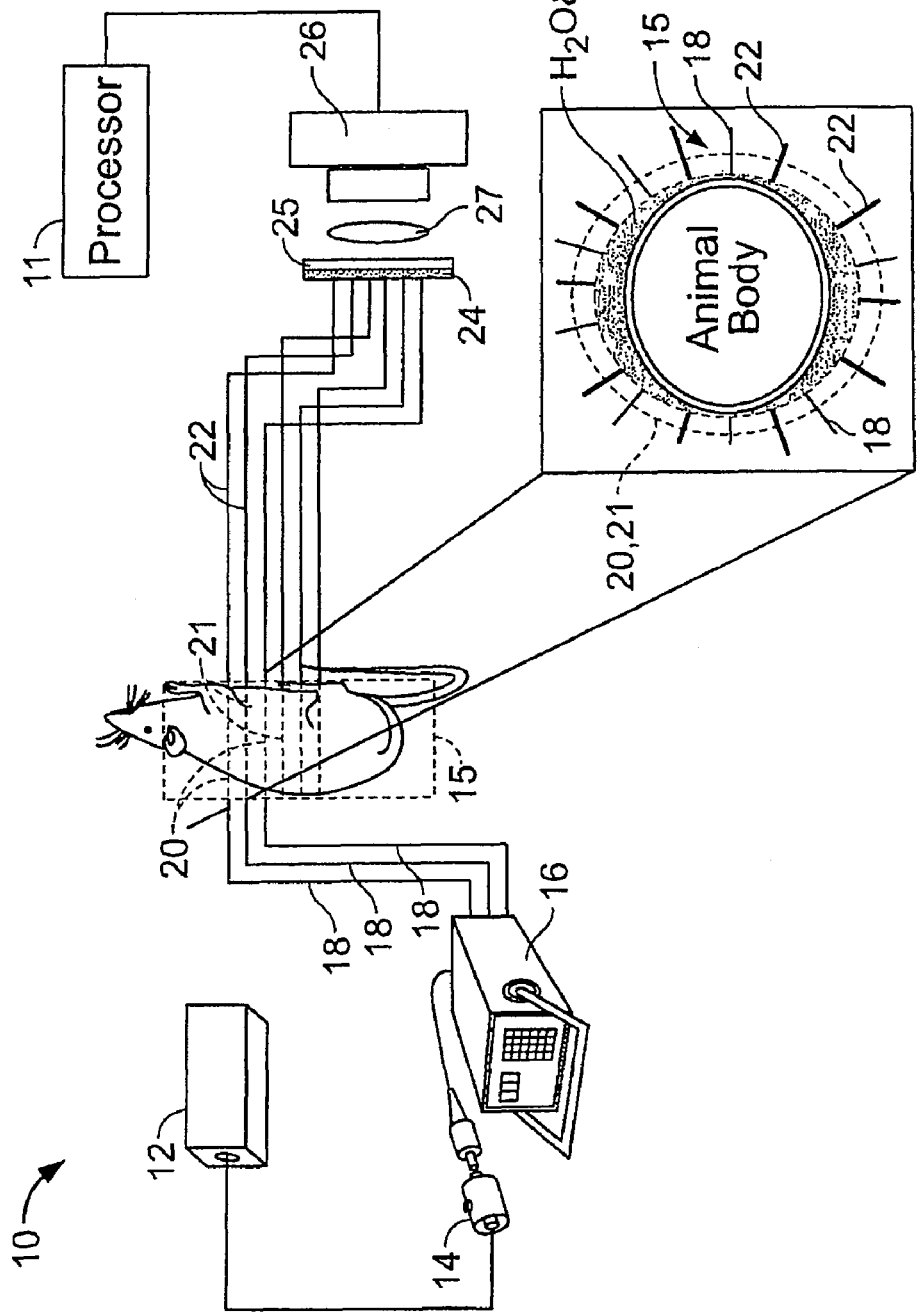
FIG. 2A is a schematic of a new three-dimensional, fluorescence tomography apparatus.

Additionally a positional device 23 can be used for optimum placement of the animal in cylinder 15 as shown in FIG. 2B. The positional device in this embodiment is simply a cylinder that fits snuggly within cylinder 15. Three positional devices 23 (cylindrical inserts) have been constructed. The first insert is constructed of Lexan® (polycarbonate) or Plexiglas®, and the second is constructed of white Delrin®, Polypropylene, or Kel-Fe. Both of these inserts have an outer diameter that exactly fits the inner diameter of cylinder 20, 21, and are 1 mm in thickness. The third insert is constructed out of Mylar® film and Kel-F® film to produce an insert with a wall thickness of 0.1 mm diameter. The advantages of this design are that the animal is stabilized during imaging and that positional accuracy with surface marks can be established for co-registration purposes.

Figure 2C:
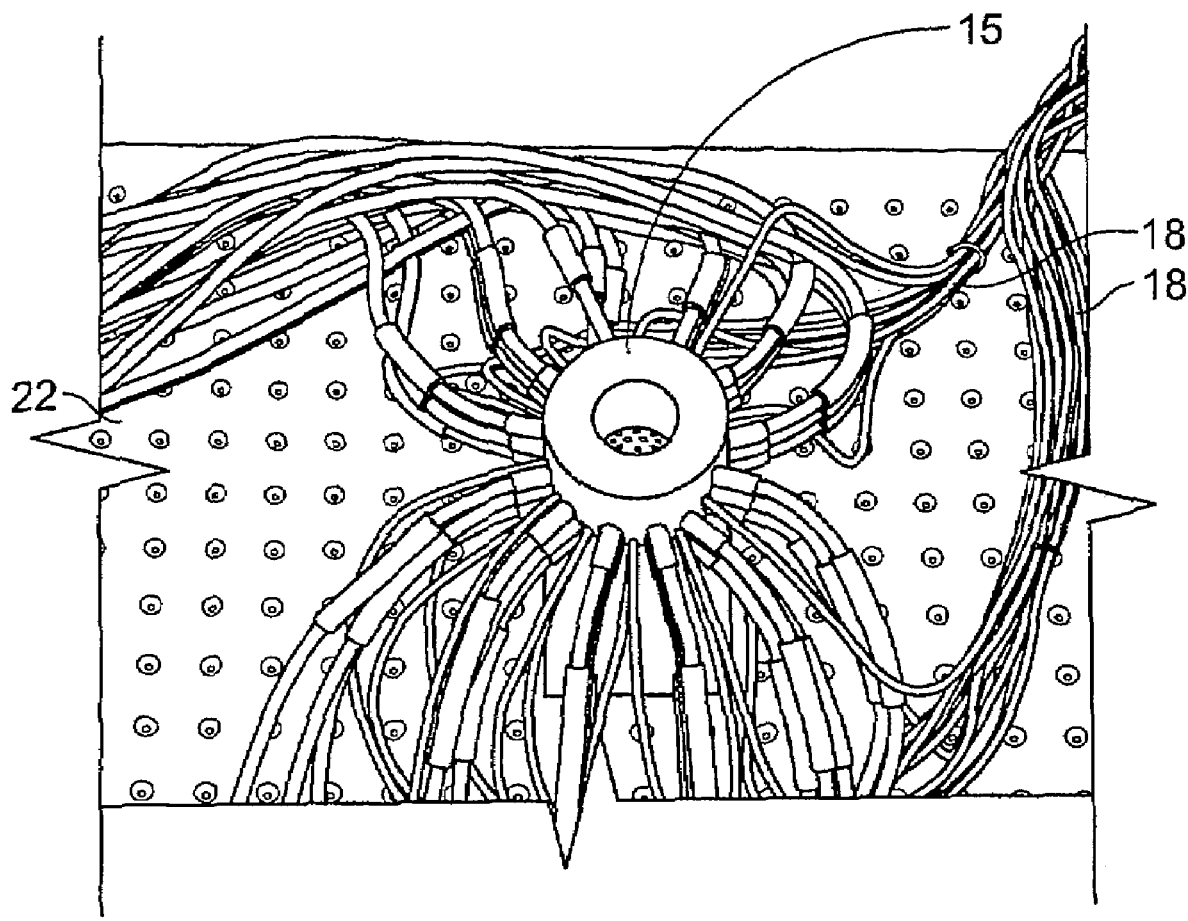
FIG. 2C is a picture of an optical imaging chamber of the system of FIG. 2A. The imaging chamber positions the source and detector fibers.

A detailed view of cylinder 15 (the imaging chamber), including both the multipoint detector array 21 and the multipoint incident illumination array 20, is shown in FIG. 2C. The source fibers 18 and detector fibers 22 are arranged so that measurements are obtained along the entire cylinder to allow for three-dimensional reconstructions. Source fibers 18 are interleaved between the detector fibers.

Figure 2E:
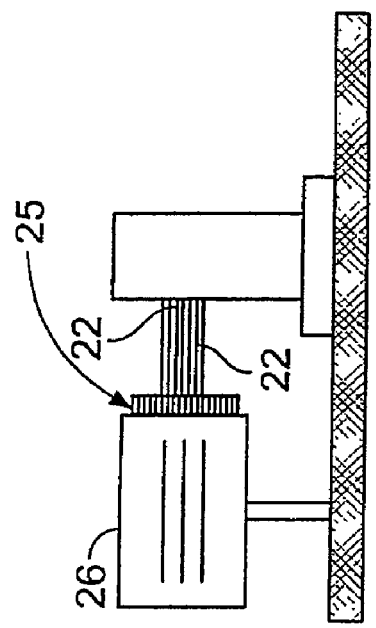
FIGS. 2D and 2E are alternative embodiments of fiber-coupling systems that can be used in the new fluorescence tomography apparatus.
Figure 2D:
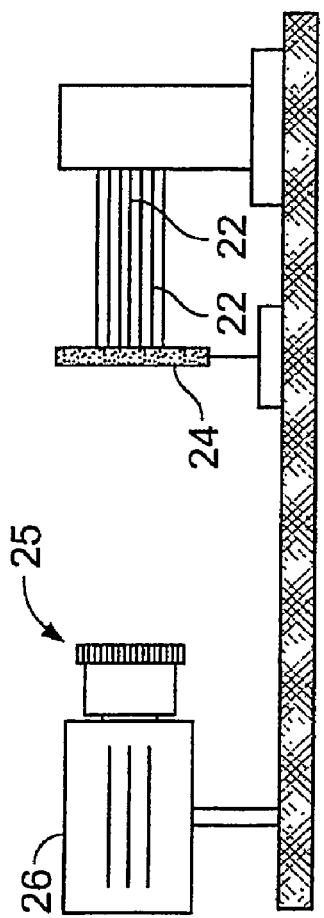

FIGS. 2D and 2E illustrate two alternative fiber-coupling systems. FIG. 2D shows the system used in FIG. 2A, in that a separate two-dimensional emitted fluorescent light array 24 is used to collect the signals of all detector fibers 22 in one plane, which is imaged by CCD camera 26 through filter 25. FIG. 2E shows a simpler embodiment in which the detector fibers 22 are directly connected to filter 25, i.e., filter 25 serves as the two-dimensional array 24.

Other embodiments of the multipoint incident illumination array are shown in FIGS. 3A to 3F. FIG. 3A illustrates a top view of the cylindrical array described above. FIG. 3B shows a planar array used for reflectance and/or transmittance mode operation. In an alternative embodiment, the array is a portion of a cylinder, e.g., in the form of a curve with a set radius as shown in FIG. 3C. On the other hand, FIG. 3D shows a schematic of a molded array, in which the ends of the light source fibers are arranged on a rigid substrate that conforms to a specific shape of a body, or are arranged on a substrate of bendable, elastic material, such as a plastic, rubber, or cloth that can secure the light emitting optic fibers, and that can be molded to conform to a body shape. FIG. 3E illustrates a belt-like, uneven array, in which the ends of the source fibers are arranged in a flexible belt that can be fastened around a patient or the limb of a patient as required. The exact positions of the light emitting points within this array can be determined and corrected for by concomitant CT, US, or MR imaging. In an alternative embodiment, the ends of the light source fibers are provided in a catheter-like device as shown in FIG. 3F.

In each of these embodiments, the ends of the detector fibers 22 can be interleaved with the ends of the source fibers 18 as in the cylinder 15 shown in FIG. 2A. Alternatively, the detector array can be separate and distinct from the incident illumination array, as long as the ends of the detector fibers are spaced in a specified geometry with respect to the ends of the source fibers. For example, in the catheter-like array, the preferred mode of use is with a separate detector array that positions the ends of the detector fibers on the outside of the body while the incident light array is positioned inside the body, e.g., to image the prostate gland, lungs, vasculature, or gastrointestinal tract.

The apparatus 10 of FIG. 2A is used with a processor 11, e.g., located in a PC, as described in further detail below. As shown in FIG. 4, such a processor 11 generally includes an input/control device 60, a memory 62, and an output device 64. The processor 11 can be an electronic circuit comprising one or more components. The processor can be implemented in digital circuitry, analog circuitry, or both, it can be implemented in software, or may be an integrated state machine, or a hybrid thereof. Input/control device 60 can be a keyboard or other conventional device, and the output device 64 can be a cathode ray tube (CRT), other video display, printer, or other image display system. Memory 62 can be electronic (e.g., solid state), magnetic, or optical. The memory can be stored on an optical disk (e.g., a CD), an electromagnetic hard or floppy disk, or a combination thereof.

A highly efficient photon collection apparatus of FIG. 2A can be built using the same or similar components as discussed above, but with the exception that dedicated detector fibers 22 are directly coupled to the CCD (as shown in FIG. 2E), versus the lens system shown in FIGS. 2A and 2D. Overall, this system design should provide at least 300% improved photon counting efficiency. Higher efficiency CCD chips will further improve photon detection.

To achieve a higher image-resolution design the apparatus of FIG. 2A can accommodate more source-detector pairs (for example 64×100) either by a lens-imaging system (FIGS. 2A and 2D) or by direct coupling (as shown in FIG. 2E). The latter system could require a larger dimension chip CCD camera to accommodate the larger detector set.

In use, baseline measurements can be obtained from the tissue at the excitation wavelength and at the emission wavelength without using the filter. Fluorescence measurements can be performed at the emission wavelength after inserting the appropriate cut-off filter.

Figure 4A:
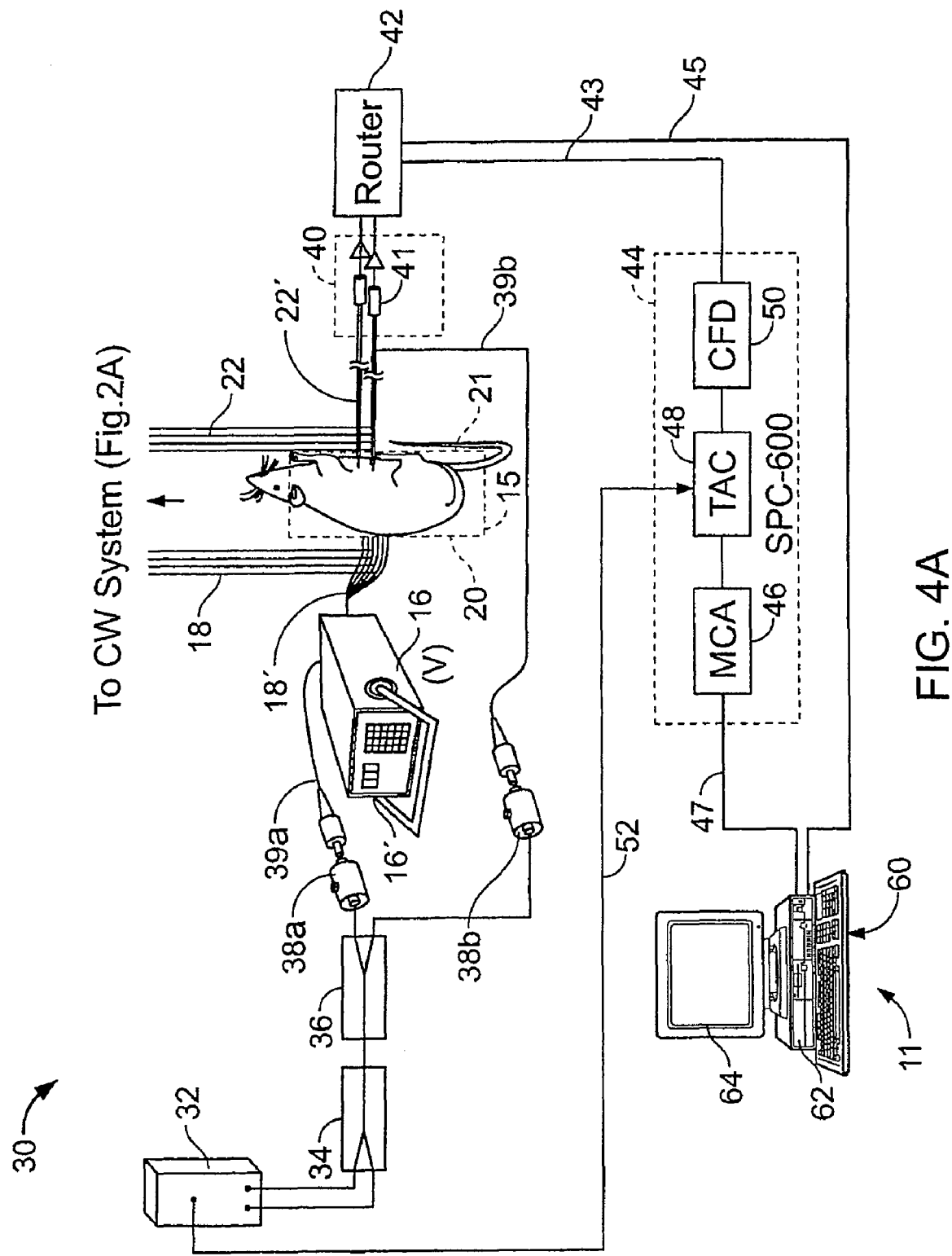
FIG. 4A is a schematic of a time-resolved, three-dimensional fluorescence-mediated molecular tomography (FMT) system that can be used in conjunction with the system of FIG. 2A.
Figure 4B:
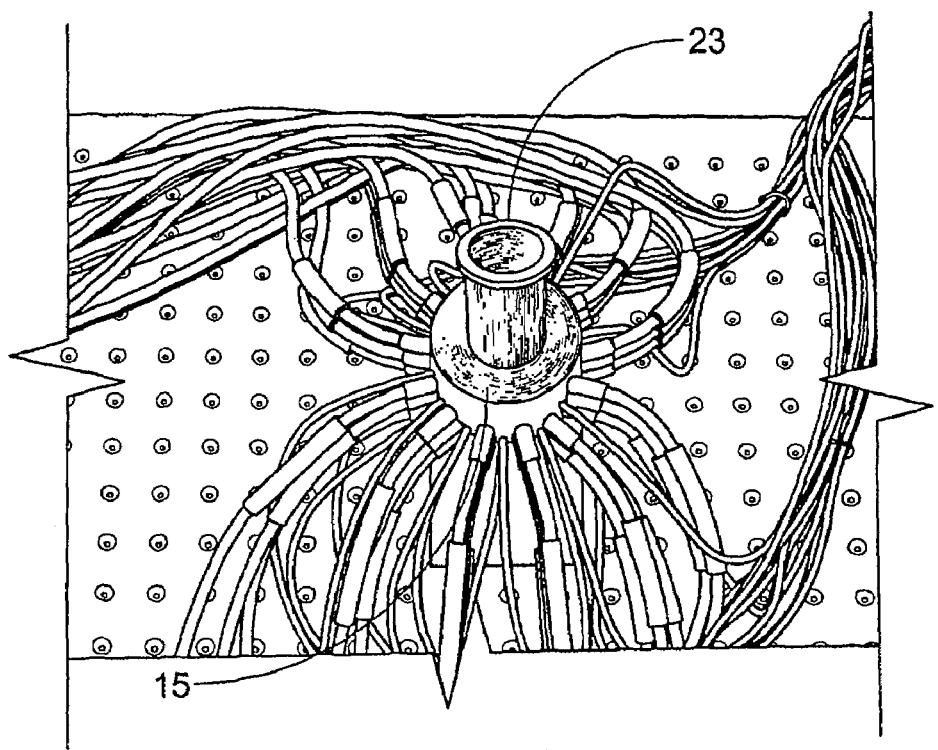
FIGS. 4B-4D are a series of photos of a positional insert used in the imaging chamber of the system of FIG. 2A (as shown in FIG. 4B), in a magnetic resonance imaging MRI coil (FIG. 4C), and holding a mouse in an MRI coil (FIG. 4D).

An add-on system that will significantly enhance the tomographic accuracy is shown in FIG. 4A. This is a time-resolved FMT imaging system 30. A 16×16 channel array is implemented together with CW measurements to yield superior reconstructions. The CW and TR system can be used independently but a benefit is achieved when the measurements obtained from both systems are combined in the same reconstruction scheme.

In general, system 30 includes a pulsed laser source 32, a wavelength coupler 34 and a wavelength splitter 36. Two sets of two pulsed laser diodes (pulse width ~70 picosecond, average power ~150 µW) are employed at the same wavelengths as the proposed CW system of FIG. 2A. The wavelengths are used time-multiplexed with 10 nm delays; they are detected simultaneously by the 16-channel single photon counting time-resolved system 44 (e.g., a SPC-600® from Pico-Quant, Berlin, Germany). The time-resolved system can share the same source fibers 18' as the CW system 18 (by connecting both CW and TR light sources to the optical switch) or use separate, dedicated source fibers. The time-resolved (TR) detection fibers 22' will be interlaced with the CW detector fibers 22. The TR acquisition will be obtained at different times than the CW acquisition to avoid cross-talk between the CW and TR systems. The relatively small source-detector array 18', 22' of the TR system (which can also be incorporated into cylinder 15) is capable of producing useful diffuse images. However, the two main contributions of the TR data will be (1) their simultaneous implementation is the inversions of Eq. 1 to obtain multi-frequency information in addition with the CW data offering a stand-alone CW-TR tomographer, but also (2) their use with the concurrent magnetic resonance (MR) information to obtain measurements of fluorescence concentration and lifetime from the tumor lesions as identified on the MR images.

The pulsed laser source 32 produces laser light that is coupled by wavelength coupler 34 and then split by splitter 36. The splitter directs 99% of the laser light along path 39a into the optical switch 16 and 1% of the light along path 39b into the detector module 40 via the corresponding attenuators 38a and 38b. The light traveling along path 39b from attenuator 38b provides a "reference signal" that is used to monitor the system's temporal drifts and signal stability. The 99% part of the laser light on path 39a that is directed to the optical switch 16 is switched in the same manner as in the CW system to selected sixteen (or more, if needed) CW source fibers 18. There is no need to use two different switches and source fibers. The same optical system used for the CW system can be used to also direct the photon pulses onto the tissue of investigation in the light chamber 15. Fibers 18 can be (but need not be) physically identical to fibers 18' and the only differentiation is made for ease of illustration to indicate their operation passing CW or TR signals. A 2-to-1 optical switch 16', e.g., provided within the Dicon switch 16, can select between the CW or TR source. However, an independent TR detector fiber array (sixteen fibers) is required to direct the collected photons at the time resolved detection system 44. Cylinder 15 is the same as in FIG. 2A. Fluorescent or intrinsic light emitted from the body is passed to the TR system as in FIG. 2A and to detector module 40. Fibers 22 indicate the detector fibers of the CW system shown on FIG. 2A.

Detector module 40 includes photomutiplier tubes (PMT) 41 that detect photons and convert single photons to electrical analog pulses. These analog pulses pass to router 42, which directs the pulses via path 43 to the SPC-600 board 44. Here the pulses are converted to digital values that indicate the time of arrival (TOA) of each coming pulse relative to the trigger pulse on path 52 coming from laser 32. Each pulse collected generates in router 42 a digital address, which uniquely marks the detection channel from which this photon was detected. This digital address is directed to the computer memory 62 via digital cable 45 and is used to store the TOA in the appropriate memory bin allocated for each individual channel. For the sixteen channels used in this embodiment, there are sixteen separate digital addresses corresponding to sixteen separate memory bins. Within system 44, constant fraction discriminator CFD 50 rejects pulses that have a very small amplitude and are probably due to photo-electronic noise, the Time-to-Amplitude Converter (TAC) converts the time of pulse arrival to an analog amplitude value, and the Multi-Channel Analyzer (MCA) converts this analog amplitude to a digital value at high speed. The output 47 of system 44 is a digital value stored in the computer memory bin that corresponds to the address carried on cable 45.

Time-resolved measurements can be used independently to obtain average background properties of the medium measured, an important input parameter for absorption, scattering, and fluorescence reconstructions. The combination of TR and CW measurements will produce more accurate forward problems for the intrinsic contrast and fluorescence reconstructions. Furthermore, the simultaneous use of CW and TR data will enhance the overall image quality and fidelity. Another alternative would be to use the time-resolved data to produce low-resolution images of background intrinsic contrast and use this information to create more accurate forward problems for the CW reconstructions for each animal.

The CW and especially the TR information can further be combined with MR imaging data to produce accurate quantitative measures of fluorophore concentration and fluorescence life-time measurements. Time-resolved methods would significantly open the spectrum to differentiate the fluorescence decay of existing and novel fluorochromes distributed in tissue. The cyanine fluorochromes that are described above typically have decay times ranging from 1 to 20 ns. While this timescale is useful for many biophysical measurements, there are numerous instances where longer decay times are desirable. For instance, one may wish to measure rotational motions of large proteins or membrane-bound proteins. Processes on the microsecond or even the millisecond timescale have been measured using phosphorescence, which displays decay times ranging from 100 ns to 10 µs. The long lifetimes of specific lanthanide metal-ligand probes will allow the use of gated detection, which could be employed to suppress interfering autofluorescence from biological samples and can thus provide further increased sensitivity.

One attractive feature is to combine molecular maps derived from FMT imaging with anatomical tomographic images, e.g., those derived from magnetic resonance (MR), X-ray computed tomography (CT), ultrasound (US) or even single photon emission tomography (SPECT) or positron emission tomography (PET) imaging. In particular, the combination with MRI or CT is preferable given the high spatial resolution of these imaging techniques. DOT imaging (absorption only) has already been combined with MR imaging (Ntziachristos et al., P.N.A.S., USA, 97:2767-72, 1999) while one of the examples in this application teaches how to combine FMT imaging with MRI. This combination with MRI will enable: (1) the validation of FMT imaging in vivo by direct comparison of the MR and optically acquired images, (2) a direct comparison of cancer appearance and detection limits based on the anatomical images obtained by T2-weighed MR images, the Gd-enhancement pattern, and molecular activity as resolved with optical imaging, and (3) the implementation of MR structural and functional information as a priori information in the optical inversion scheme to obtain highly accurate measures of localized fluorophore concentration and lifetime. The combination of MRI and FMT also improves quantitation accuracy of fluorophore concentration and lifetime. Overall, molecular probing will improve the detection accuracy and introduce the ability of molecular target assessment.

To avoid interference with the magnetic field, non-magnetic fiber bundles can be used to transport excitation and emission light to and from exciter/detection systems to the patient. For human applications, available commercial or custom-built MRI coils available in any MR facility can be used. The MR coils can be coupled to one of the geometries described in FIGS. 3A-3F depending on the application. To identify the exact position of the multi-point incident illumination array and detector arrays, coupled to the skin, MR or CT imaging itself can be used. Knowledge of the spatial location of source fiber ends and detector fiber ends on uneven surfaces improves optical reconstructions. The skin-coupled fibers as shown in, e.g., FIG. 3E, or internally placed fibers, e.g., endorectally using the array of FIG. 3F, can be detected by imaging if the arrays are constructed of materials that are uniquely detectable, e.g., materials that include microreference phantoms filled with magnetic/x-ray absorbing compounds, certain chemicals, or plastics. For example, to identify the position of the multipoint incident illumination array and detector array cylinder and the optical fibers on the MR images, small reference capillaries filled with water and $CuSO_4$ can be attached to the cylinder to appear as bright spots on the MR images.

Figure 4C:
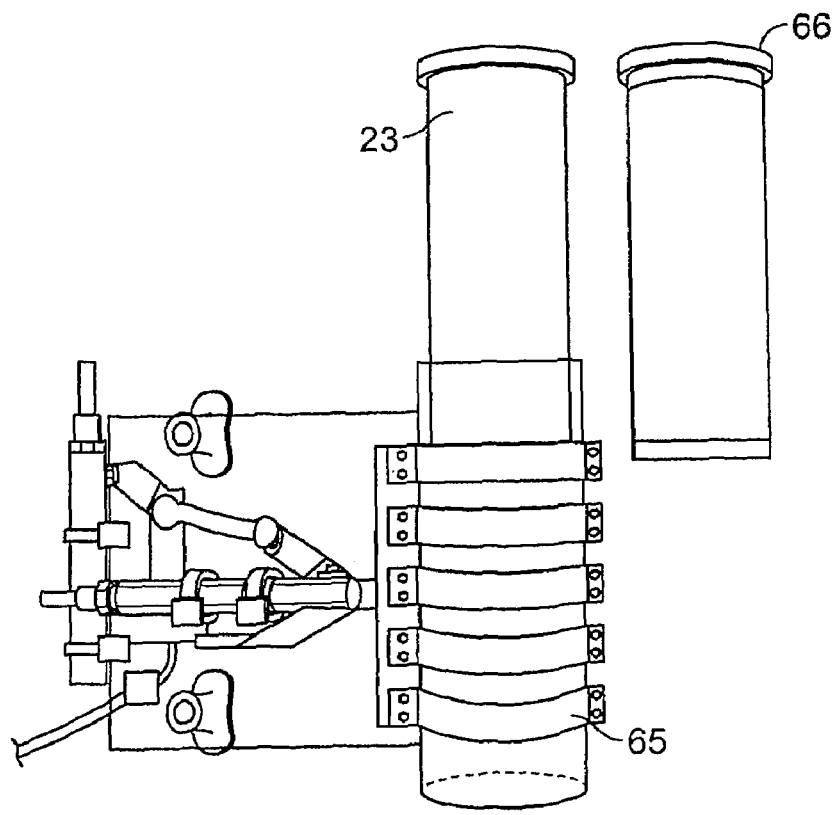
Figure 4D:
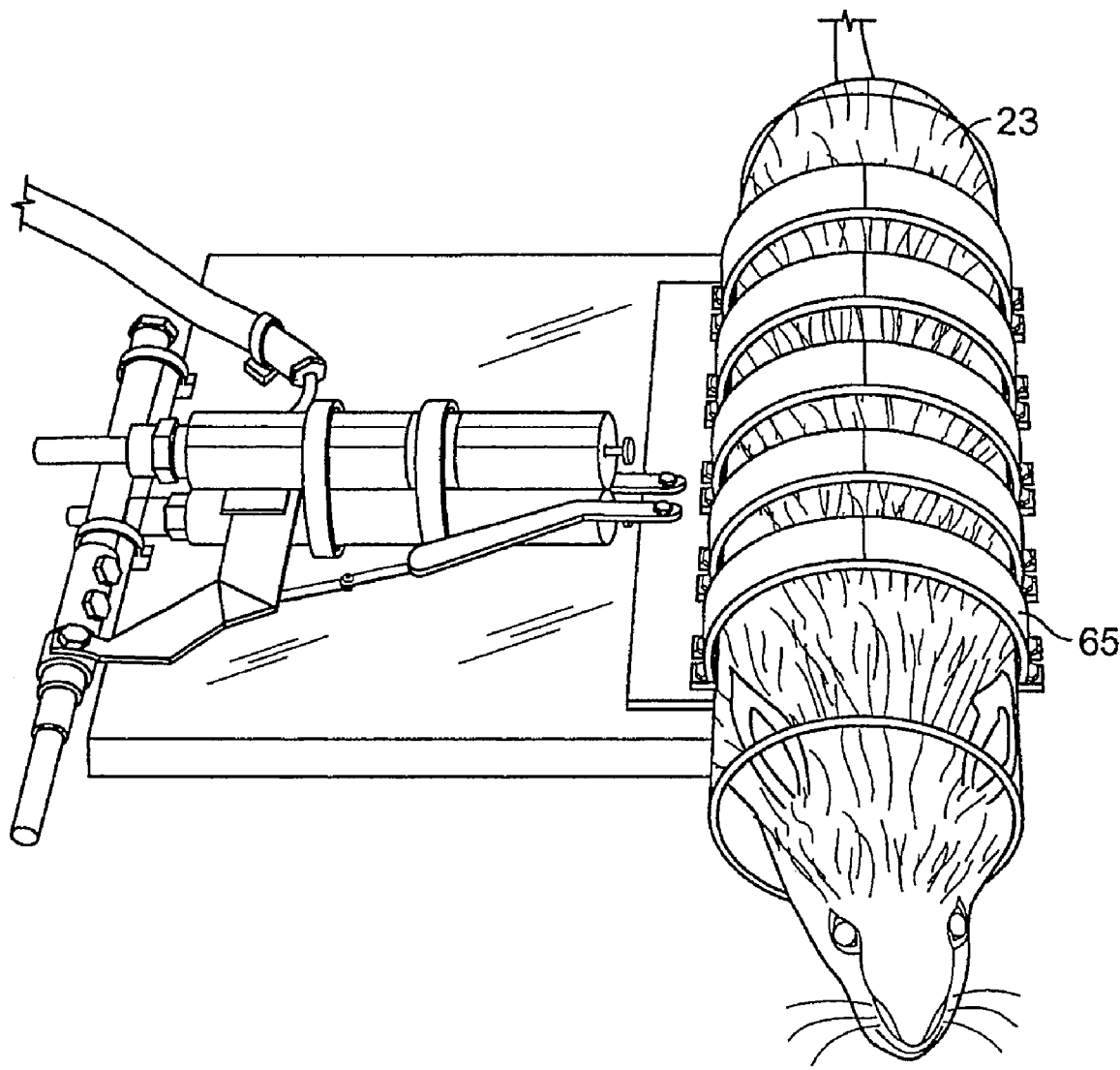

FIGS. 4C and 4D are representations of a magnetic resonance (MR) coil 65 used for co-registration purposes. The coil 65 is specially built to accommodate the animal insert 23 shown in FIG. 2B. Two implementations are considered. In one embodiment, after FMT imaging is performed, insert 23 containing the animal is removed from the imaging chamber 15 and positioned within MR coil 65. One or more specially designed glass capillaries 66 (1 mm glass tubes filled with water and copper sulfate) are attached to insert 23 and enable the MR and FMT images to be co-registered. Such a fiducial marker is visible as a bright circular spot on the left side of the MR image in FIG. 8A (discussed below). FIG. 4D shows a mouse positioned within positioning insert 23, within MRI coil 65. The second embodiment has the coil built directly around imaging chamber 15 of FIG. 2A so that concurrent MR and FMT examinations can be performed.

Data Collection

Figure 5:
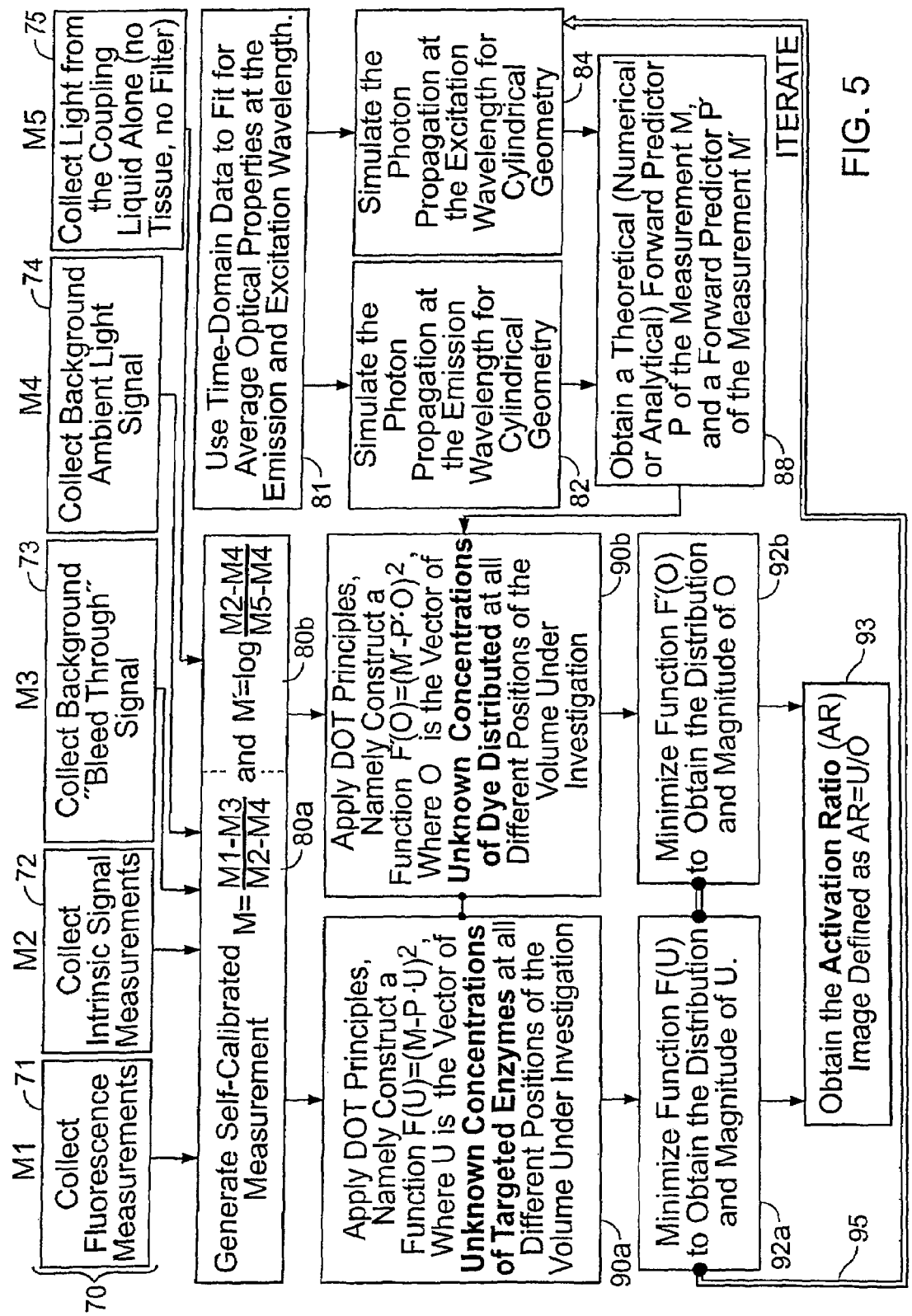
FIG. 5 is flow chart of the steps used to process analog fluorescent and intrinsic (absorption) signal data in three dimensions to provide (i) a vector U of concentrations of activated fluorescent probes within a given volume, (ii) a vector D of concentrations of non-activated and activated probes, and (iii) a vector AR which is the ratio of activated over total NIRF probe.

Five sets of measurements M1-M5 for each of the TR and CW used are obtained as shown in the flowchart of FIG. 5. Although subsets of the collected data can be used depending on the requirements of the application, the highest accuracy is obtained when the full data set is utilized.

As shown in FIG. 5, there are five sets of simple measurements (M1, 71; M2, 72; M3, 73; M4, 74; and M5, 75) to be obtained in initial step 70. In the first step 71, the fluorescence measurement M1, is obtained. This is a measurement where the source is scanned at multiple positions, and the detector acquires the light emitted from the tissue with the band-pass filter on, so that only the emission wavelength (fluorescence) is collected. In step 72, the second measurement, M2, is made as in step 71, but without the band-pass filter to acquire the intrinsic signal from the tissue at each wavelength. If the fluorescence signal is very small compared to the intrinsic signal no filter is required. However, if the fluorescence (M1) from the tissue of investigation is more than 1% of M2, then a cut-off filter is used to reject the fluorescence wavelength. In step 73, measurement M3 is made to acquire the amount of intrinsic light that passes through the fluorescence filter (high-pass filter) used in step 71. To achieve this measurement, the tissue to be investigated is removed from the cylinder, and a measurement is made from the matching fluid with the fluorescence filter (band-pass filter) on. This measurement is also used to acquire the contribution of ambient light and other photonic and electronic noise on a per source basis. In step 74, measurement M4 is obtained with all sources turned off to acquire only the ambient (background) light and CCD noise. In step 75, measurement M5 is obtained without a filter and without tissue at the excitation and the emission wavelength using appropriate laser diodes. This measurement acquires the background signal.

Practically, for CW measurements each of M1, M2, M3 and M5 vectors is a series of Ns images (where Ns is the number of sources used). M4 is a single image of background noise. For the TR measurements, each of M1, M2, M3, and M5, is a set of Ns×Nd×2 wavelengths where Nd is the number of detectors.

Composite Measurements (CM)

These simple measurements are combined to create self-calibrated (or composite) measurements of fluorescence M (step 80a) and intrinsic contrast M' (step 80b), i.e:

$$M=(M1-M3)/(M2-M4) \qquad \text{Eq. 1}$$

And $$M'=\log((M2-M4)/(M5-M4)) \qquad \text{Eq. 2}$$

Although not explicit in the above equation, the measurements M1-M5 are functions of the frequency. Therefore CW and TR data (after Fourier transformation) are handled in exactly the same way. The rationale for this construction is that these composite measurement vectors are independent of instrumental gain variation, such as differences in the attenuation between different source or detector fibers and inhomogeneities within the CCD chip. Furthermore these vectors subtract from the actual measurements systematic errors such as background noise (M4) or high-pass filter imperfectness (M3). Although several ways would exist to calibrate the measurements, these particular constructions are directed after the theoretical predictions of fluorescent and intrinsic signals, which is a necessary step for quantitative reconstructions. This point is elucidated in the following paragraph.

Depending on the specific application, other alternatives can be used to construct self-calibrated composite measurements. For example in dynamic imaging, where the fluorophore concentration and activation is monitored as a function of time, measurement M5 could be substituted by measurement M2 at time 0, preferably before the NIRF probe has been administered to the animal. Therefore the fluorochrome absorption can be accurately monitored as a difference signal from intrinsic tissue absorption.

Construction of the Forward Problem

To perform tomographic measurements a theoretical prediction of our composite measurements (CM) (i.e., the measurement M and the measurement M') is required, which is referred to as the "forward predictor" (P) or the "weight matrix." The P and CM are combined to produce molecular tomographic measurements as described in the following section. Herein the specific theoretical constructions that adapt tomographic principles of diffraction tomography (Kak & Slaney 1988) are presented.

The P for fluorescence is constructed based on a modified Born prediction of the forward problem (Li et al., 1996). Generally the medium is assumed to contain a weakly absorbing distribution of fluorophores. The fluorophores will be excited by this photon distribution and act as a secondary point source of fluorescent light. The fluorophores as two-level quantum systems and saturation effects are ignored because of the small concentration of NIRF probes that are administered. Then the standard Born expansion for fluorescence measurements can be written as:

$$\phi_{fl}(\vec{r}_d, \vec{r}_s) = \int_V g_{fl}(\vec{r} - \vec{r}_d) \frac{\sigma c N_t(\vec{r})}{1 - i\omega\tau} \phi_0(\vec{r}, \vec{r}_s) d\vec{r} \qquad \text{Eq. 3}$$

where $\phi_{fl}(\vec{r}_d, \vec{r}_s)$ is the detected fluorescence fluence at position $\vec{r}_d$ for a source at position $\vec{r}_s$, $\phi_0(\vec{r}, \vec{r}_s)$ is the established photon fluence in the homogeneous medium due to a source at position, and $g_{fl}(\vec{r} - \vec{r}_d)$ is a function that describes the propagation of photons in the diffuse medium at the emission wavelength. $N_t(\vec{r}) = [F] \cdot \gamma$ is the unknown concentration of the fluorophore F multiplied by the fluorescent yield $\gamma$ at a position $\vec{r}$, $\sigma$ is the absorption cross-section of the fluorochrome, c is the speed of light in the diffuse medium, $\tau = 1/\Gamma$ is the fluorescent lifetime and $\omega$ is the modulation frequency of the source light intensity. For sources of constant intensity $\omega = 0$. Our construction of the forward predictor (P) in step 88, which predicts measurement M (step 80a) is:

$$M = \frac{M1 - M3}{M2 - M4} \qquad \text{Eq. 4}$$
$$= \frac{1}{\phi_0(\vec{r}_d, \vec{r}_s)} \int_V g_{fl}(\vec{r} - \vec{r}_d) \frac{\sigma c N_t(\vec{r})}{1 - i\omega\tau} \phi_0(\vec{r}, \vec{r}_s) d\vec{r}$$

This is a modified Born expansion that normalizes the standard Born expansion with the incident field $\phi_0(\vec{r}_d, \vec{r}_s)$. Therefore, the gain of sources and detectors are canceled out for each source-detector pair independently.

For intrinsic contrast reconstructions, the forward predictor P' is determined (in step 88) using the Rytov expansion in the frequency domain, as described, e.g., in O'Leary et al., Opt. Lett. 20:426-428, 1995; and Ntziachristos et al., Proc. Natl. Acad. Sci., USA, 97:2767-72 2000. Then the measurement M' (step 80b) can be written as:

$$M' = \log \frac{M2 - M4}{M5 - M4} \qquad \text{Eq. 5}$$
$$= \frac{1}{\phi_0(\vec{r}_d, \vec{r}_s)} \int_V g_0(\vec{r} - \vec{r}_d) o(\vec{r}) \phi_0(\vec{r}, \vec{r}_s) d\vec{r}$$

where $\phi_0(\vec{r}, \vec{r}_s)$ is the incident field from the source at position $\vec{r}_s$ to position $\vec{r}$ and $o(\vec{r})$ is the vector of the unknown absorption and diffusion coefficients changes relative to the assumed homogeneous background medium.

The functions $g_{fl}$ and $\phi_0$ are calculated by simulating photon propagation at the emission (step 82) and excitation (step 84) wavelengths for the specific imaging chamber geometry and diffusion theory. This can be achieved either analytically or numerically. To perform these simulations, knowledge of the tissue average optical properties in the wavelengths of interest are required. The optical properties can be obtained by fitting all the intrinsic contrast TR measurements to the diffusion model for the appropriate geometry. Analytically, standard methods can be applied (adapted for the cylindrical geometry) as described in Li et al., Appl. Opt., 36:2260-2272 (1997). Here however, we propose to use a homemade finite-differences numerical algorithm that solves the diffusion approximation for a cylindrical geometry using a partial boundary condition (Arridge, Inverse Problems, 15:R41-R93, 1999), which accurately models even small source-detector separations. This must be used to obtain more accurate propagation models for the smaller scale problem. The only unknown in Eq. 4 and Eq. 5 are then the distribution of the fluorophore or the absorption and diffusion coefficients respectively. The minimization of Eqs. 4 and 5 is described in the next section.

Data Inversion

Both fluorescence and intrinsic contrast reconstructions are based on the creation of a function that is subsequently minimized. In step 80a the composite measurement M is used to construct the function $F(U) = (M - P \times U)^2$ and in step 80b the composite measurement M' is used to construct a function $F'(O) = (M' - P' \times O)^2$, where U is the vector of unknown non-quenched (activated) fluorochrome concentration and O is the vector of unknown absorption and diffusion distributions. The absorption distribution can be converted to flurochrome concentration via the Beer-Lambert Law. The matrices P, P' are described in the previous section. In steps 92a and 92b, the functions F(U) and F'(O) are minimized to obtain the distribution and magnitude of U and O, respectively. The minimization is obtained using algebraic reconstruction techniques although any other minimization method can me used to find the solution of the constructed functions.

Iteration is not necessary when only small amounts of fluorochrome are activated. This is the most typical case. However, if for certain applications large concentrations of activated fluorochrome are expected (namely the absorption perturbation yielding more than 10% variation in the intrinsic signal), then iterative steps are necessary. The first step of the iterative process 95 assumes a homogeneous background with the average optical properties of the medium of investigation. Subsequent steps use images U and O as background maps in the creation of matrices P, P'. When iteration is used, the creation of P, P' using numerical solutions of the diffusion equation is necessary. Iteration is also necessary when the background distribution of the fluorochrome is comparable to the contrast obtained from localized areas of high accumulation such as the tumor. Iteration is typically stopped when each iteration step does not significantly change the calculated result.

Molecular Maps

The new systems and methods enable the quantitative, three-dimensional calculation of molecular and molecular-activation maps. The resolved image U contains the concentration of fluorescing or activated fluorochrome, whereas the absorption image contained in O is a quantitative representation of the total fluorochrome concentration (quenched and de-quenched). The ratio of activated over total fluorophore concentration is the activation ratio map (step 93):

$$AR = U/O \qquad \text{Eq. 6}$$

which represents the amount of activation normalized by the amount of fluorochrome actually distributed in the volume of investigation. For volumes in which the absorption is zero the ratio AR is not defined. This is natural, since for zero fluorochrome distribution there should be no activation. Therefore, the ratio AR is by default applied only in the volume elements with non-zero absorption.

Figure 6A:
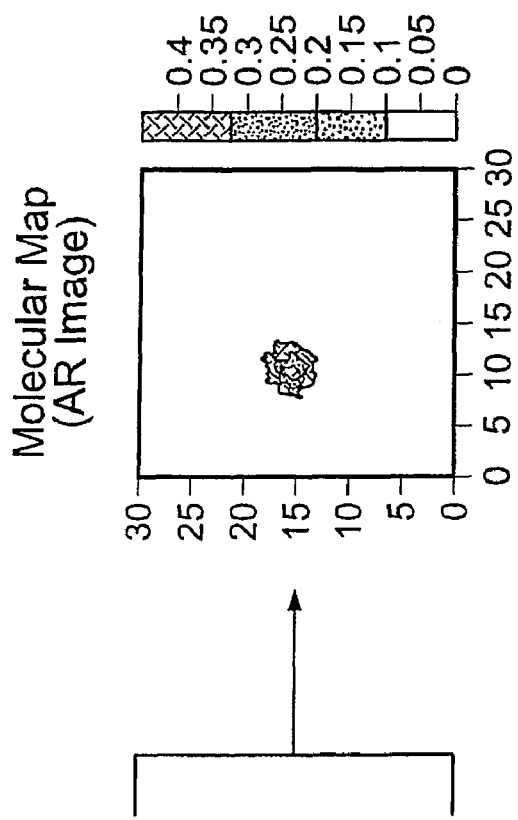
FIGS. 6A-6C are a series of images representing an absorption map (6A), a fluorescence map (6B), and a molecular map showing the absorption ratio (AR).
Figure 6B:
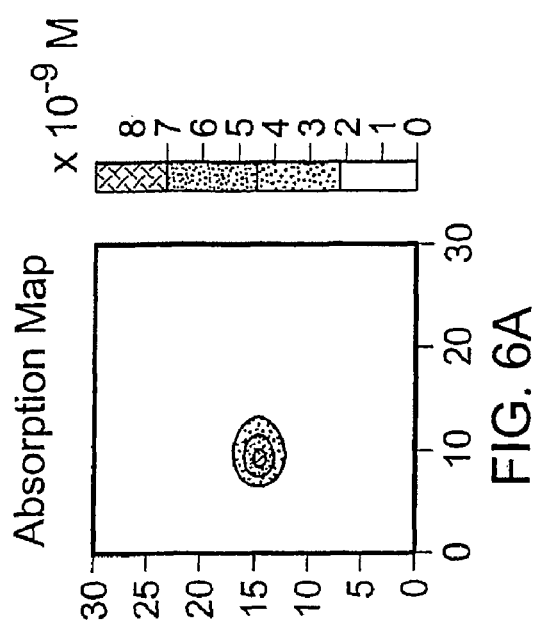
Figure 6C:
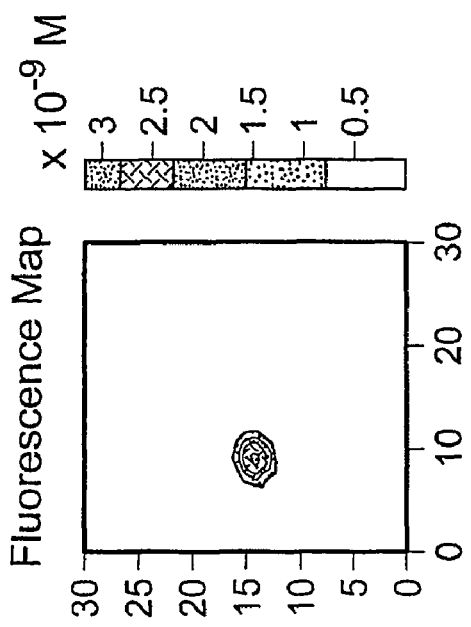

The generation of a molecular map (reporting the activity of the enzyme trypsin) is shown in FIGS. 6A-6C. A molecular map is a representation of an endogenous process or molecule. A molecular map (MM) is best described as MM=k*AR, where k is a constant; i.e., MM=k*(U/O).

FIG. 6A is an image of an absorption map, showing the concentration of a molecular probe sensitive to degradation by trypsin. The bright spot in FIG. 6A is a representation of the total amount of the probe, both the quenched and the unquenched fractions. FIG. 6B is the corresponding fluorescence map, which measures only the fraction of de-quenched (i.e., enzyme activated) trypsin sensitive probe. FIG. 6C provides the AR image, or "molecular map," displaying the "fluorescence activation" as an image where the bright spot is directly proportional to the amount of added trypsin enzyme used in this experiment.

EXAMPLES

The invention is further described in the following examples, which do not limit the scope of the invention described in the claims.

Example 1

FMT Images of a Phantom

Figure 7A:
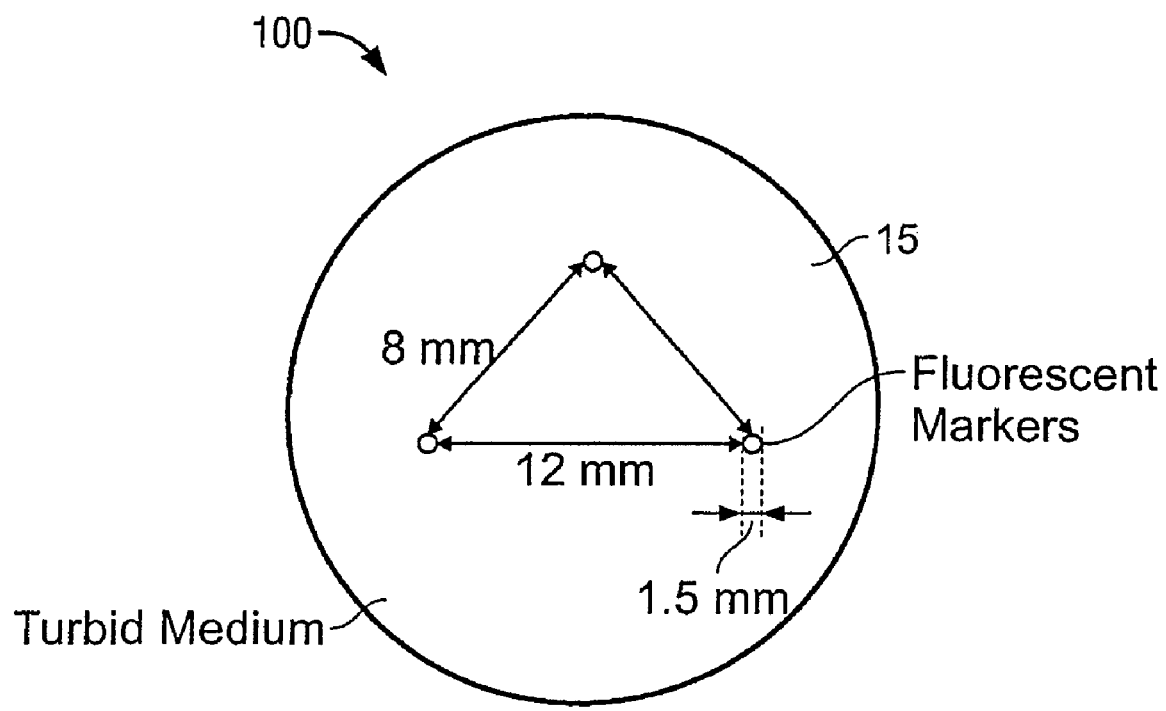
FIGS. 7A and 7B are schematic diagrams illustrating absorption imaging at high resolution.

In one embodiment, phantom experiments were performed to verify the three-dimensional position and accuracy of measurements. The experimental set-up is illustrated in top view in FIG. 7A. Briefly, a phantom 100 containing 3 capillary tubes (1 mm internal diameter) 103, was constructed using a triangular geometry and inserted into the optical chamber (15 in FIG. 2A) containing a turbid medium 102 (0.5% Intralipid® in water). The capillaries 103 were separated 8 and 11 mm from each other as shown in FIG. 7A, and were coated with a black fluorochrome to maximize absorption. The capillaries were imaged three dimensionally.

Figure 7B:
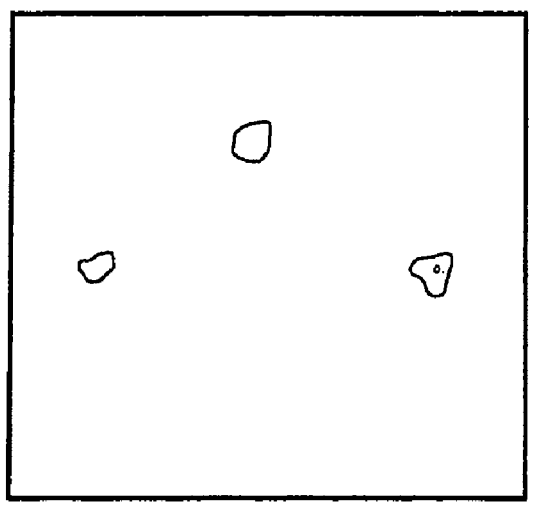

FIG. 7B depicts the reconstructed image 110 at a plane perpendicular to the longitudinal axis of the imaging chamber 15, at about the middle of the three-dimensional volume imaged. The high contrast allowed for high-resolution imaging of the three capillaries with high positional precision. The reconstruction mesh used was $0.8 \times 0.8 \times 2$ mm$^3$. The reconstruction used 24 sources×36 detectors.

Example 2

FMT Images of Trypsin Activity Over Time

Figure 8A:
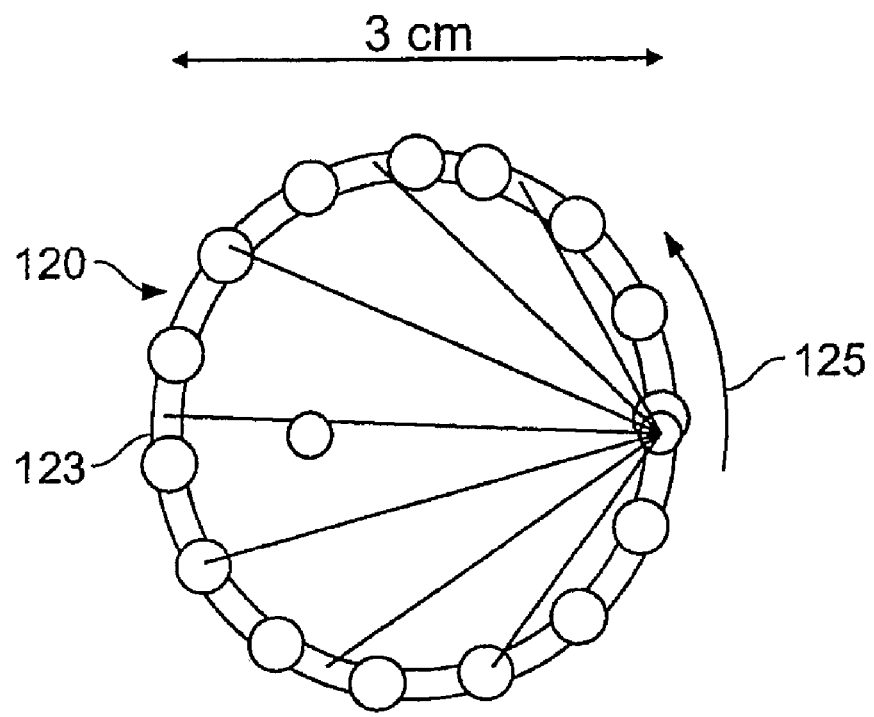
FIGS. 8A and 8B are schematic diagrams of the experimental setup to image enzyme activity in three dimensions in a tissue-like medium using a circular multipoint incident light array in cross-section (8A) and in three dimensions (8B).
Figure 8B:
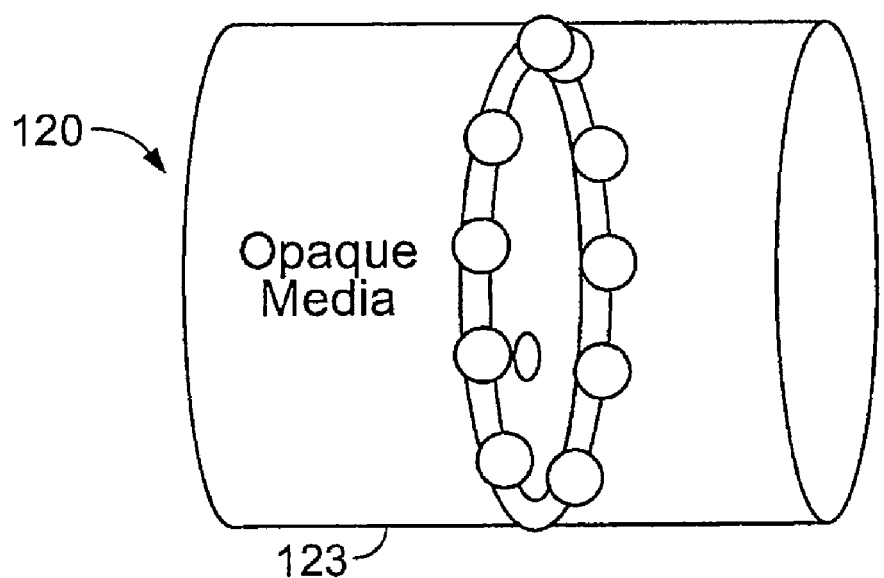

In another experiment, quantitative, spatially localized information on fluorescence activation was obtained as a function of time. As shown in FIGS. 8A and 8B, a 3 mm tube 123 was immersed in a tissue-like fluid (Intralipid®) to form phantom 102. The tube contained 1.5 μM of a Cy5.5 probe, which was activated by the addition of the enzyme trypsin into the tube at time 0. Only a single plane was imaged in this experiment by sequentially illuminating each of twelve light emitting points in the direction of curved arrow 125. FIG. 8B illustrates the phantom in a three-quarter view.

Figures 8C, 8D:
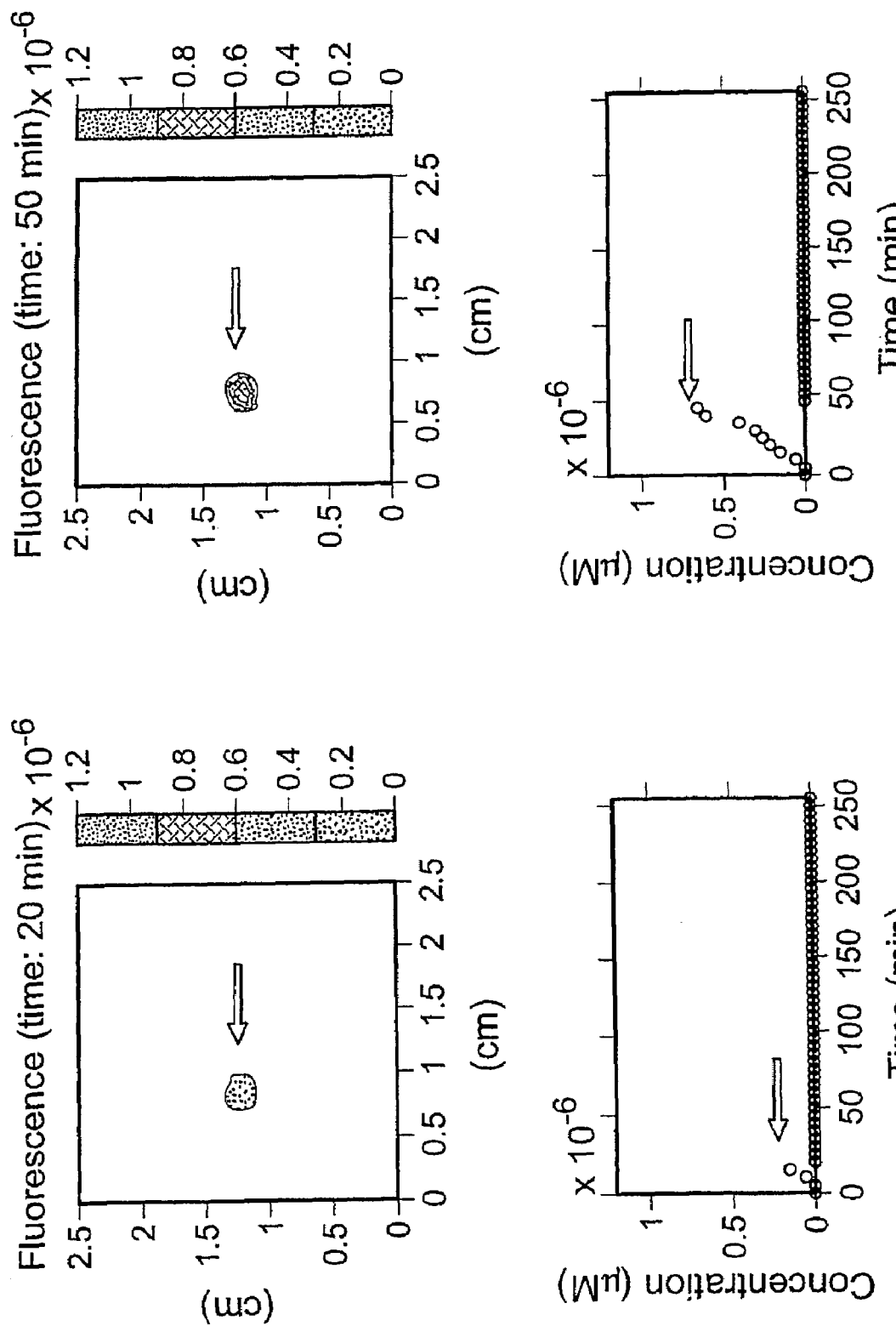

FIGS. 8C to 8F illustrate a series of axially reconstructed frames obtained at different time points. The frames show the probe activation as a function of time. For example, as shown in FIG. 8C, at 20 minutes after trypsin was added to the capillary, only ~20% of the probe had been activated. However, as shown in FIG. 8F, at 200 minutes after the enzyme was added, ~75% of the probe had been activated. Each frame was acquired by sequentially directing light in each one of twelve source fibers located on the same plane along the cylinder. For each source, the CCD acquired light from the detector fibers for 5 seconds. The total acquisition time per frame was therefore 1 minute (12 sources×5 seconds each).

Example 3

Multiple Co-Registered Images of Cathepsin B Activity in a Mouse

Figure 9A:
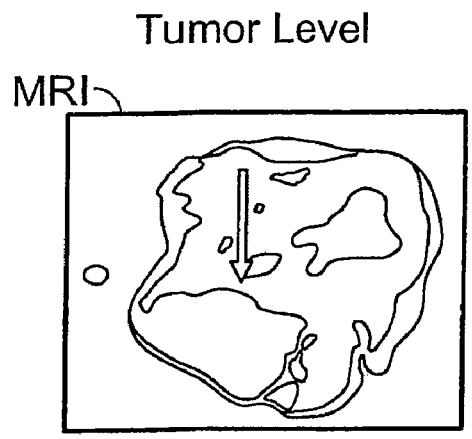
FIGS. 9A-9C are a series of images from a live mouse imaged at a cross-section through the region of an implanted human tumor.
Figure 9B:
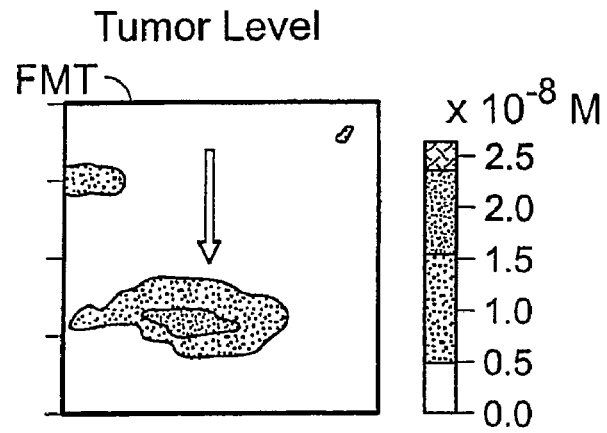
Figure 9C:
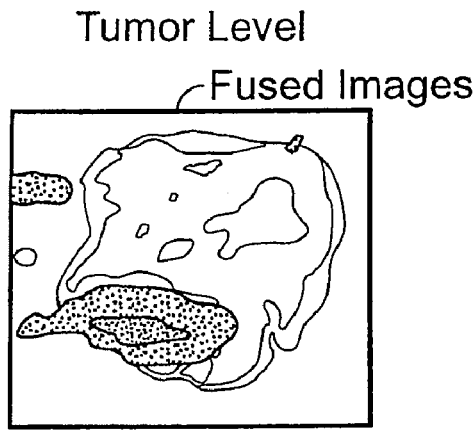

In another experiment, combined MR/FMT imaging was used to obtain maps of cathepsin B protease activity in human tumors implanted in nude mice (FIGS. 9A-(C)). The tumors were cathepsin B rich HT1080 fibrosarcoma, which had been implanted into the mammary fat pad 7-10 days prior to the experiment. The animals received an IV injection of a cathepsin B sensitive imaging probe (Weissleder et al., Nat. Biotechnol., 17:375-378, 1999) at 24 hours prior to the imaging experiments. The animals were anaesthetized with an intraperitoneal injection of 90 mg/kg ketamine and 9 mg/kg xylazine and were placed into the insert 23 shown in FIG. 2B. The insert and animal were placed into the imaging chamber 15 and measurements M1, M2, M3, and M4 were obtained.

Subsequently, the mouse within the insert was removed from the imaging chamber. Fiducials (as described herein) with water were attached to predetermined positions on the periphery of the insert. The insert was subsequently placed in the MR coil and a set of axial T2-weighted imaged were obtained. The role of the fiducials was to identify on the MR images the position of selected source and detector fibers for later co-registration of the images. The fiducial (a glass capillary tube arranged longitudinally along the outside cylinder wall) shown on the slices of FIGS. 9A, 10A, and 11A as a bright spot on the left side of the image, for example, indicates the position of detectors 1, 13, and 25 on the corresponding slices.

Figure 10A:
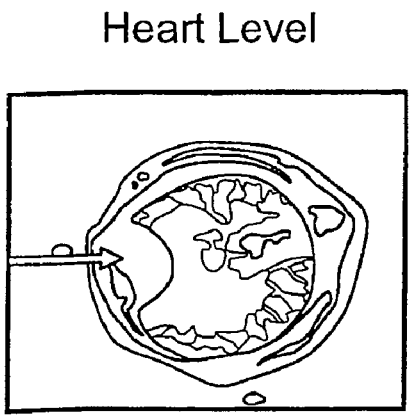
FIGS. 10A and 10B are a pair of images, MR and FMT, respectively, from a live mouse imaged at a cross-section at the level of the heart.
Figure 10B:
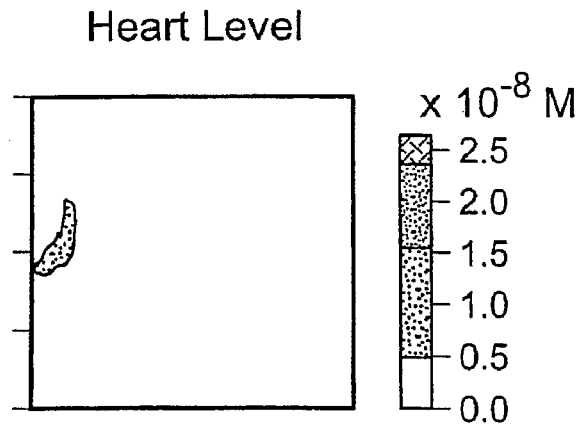
Figure 11A:
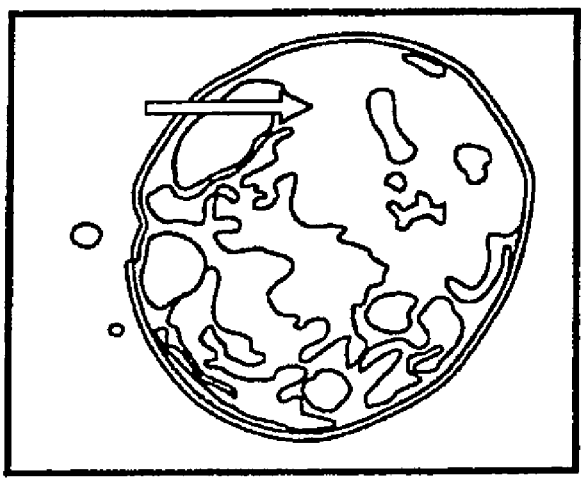
FIGS. 11A and 11B are a pair of images, MR and FMT, respectively, from a live mouse imaged at a cross-section at the level of the kidney.
Figure 11B:
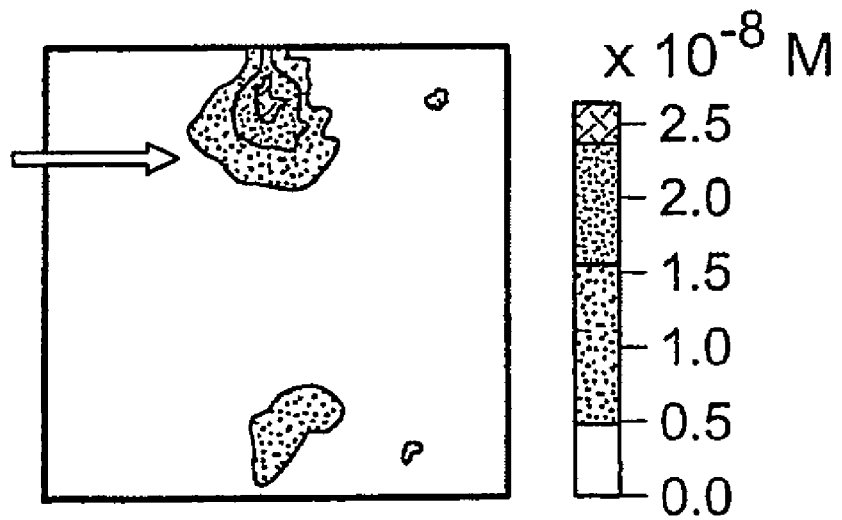

The results show an MR image (FIG. 9A), a cathepsin B molecular map (FMT)(FIG. 9B), and one of the MR slices fused with the FMT image to produce a combined MR/molecular map (FIG. 9C). There is excellent congruence of optical and MR contrast from the images obtained at the tumor level. The tumor demonstrates strong molecular activity of cathepsin B (fluorescence activation), corroborated by immunohistochemsitry and Western blotting. The co-registration of the fluorescent activation and T2 image are shown on the fused image in FIG. 9C. The remaining two rows of images are slices that show cathepsin B absence and/or presence in other tissues. Specifically, FIGS. 10A and 10B show an MR image and FMT image at heart level, respectively. As expected, there is no cathepsin B activity in the lung and heart, and thus nothing lights up on the FMT image in FIG. 10B. FIGS. 11A and B show an MR image and FMT image at kidney level, respectively. The fluorochrome appearing in the kidney is likely excreted excess, and does not reflect cathepsin activity.

This is an example where a subset of the full measurement array is used (only M1 through M4 CW measurements, no M5 and no TR data) to produce a enzymatic activity image that conveys useful information for the clinical examples describes in the following examples. Moreover, this series of images in FIGS. 9A to 11B confirms that the new methods and systems can be used to generate multi-slice images of living animals.

Example 4

Molecular Maps

To demonstrate the use of producing molecular maps we have used the set-up of Example 3, but acquired the full array of M1 through M5 measurements in CW mode. The optical properties of Intralipid® were independently measured with a time-resolved system. Then a fluorescence map (FIG. 6B) collected 50 minutes after trypsin activation and an absorption map (FIG. 6A) were constructed according to the algorithm described in the flowchart in FIG. 5. The molecular map (AR image) calculated according to step 93 is shown in FIG. 6C and demonstrates 40% activation of the enzyme sensitive probe 50 minutes after activation.

Example 5

Enzyme-Specific Probes

We have synthesized a number of different sensitive enzyme-specific imaging probes useful for FMT imaging. The probes are specific for cathepsin D, cathepsin K, the enzymatically active form of prostate specific antigen (PSA), and matrix metalloprotease-2, among other enzymes. The specificity of these probes was shown by incubation with purified or recombinant human enzymes and by measurement of fluorescence activation in a fluorometer. The NIR fluorophore Cy5.5 was used as a quenched reporter in all of these probes. Any of these probes can be used in animals and human patients as described herein to measure enzyme activity within deep tissues (both normal and diseased tissues). For example, MMP-2 activity can be measured in tumors before and after treatment with an MMP-2 inhibitor (e.g., Prinomastat®). Such measurements of molecular target assessment are useful for rapid drug efficacy screening in vivo in animal models. Moreover, such screening methods can be used to assess the efficacy of a particular therapy in a specific patient.

Example 6

Clinical Use

The new FMT methods are expected to have broad clinical implications. One use is for early detection of disease at a stage when molecular abnormalities are present, but have not yet led to phenotypic abnormalities (e.g., mutations in cancers which have not yet produced a tumor mass). Another use is for molecular target assessment in diseased tissues (1) to determine if a given target is present in a patient (e.g., level of expression of a protease), (2) to determine whether an experimental drug has an effect on its intended molecular target in vivo, (3) to individualize and tailor treatments for a given patient, and (4) to optimize the dose of a given molecular drug for a given patient. In this sense, the new FMT imaging methods are an adjunct to testing drug efficacy. Such measurements would also be of value in a clinical setting to determine the effects of enzyme inhibitor drugs, receptor blockers, and other molecular drugs. The methods could be used to monitor a wide variety of disease including cancer, cardiovascular disease, AIDS, infection, immunologic diseases, inflammation, dermatological and ophthalmic diseases, neurodegenerative disease and others.

Example 7

Multiple Probes

The new FMT methods can be performed with the concomitant use of multiple molecular probes (each with their own, specific excitation and emission wavelengths) to report multiple molecular abnormalities during the same FMT imaging acquisition. The described system can be adapted by adding one or more new laser sources to excite the additional fluorescent molecular probes. Imaging signals are collected through appropriate filter systems, making sure that there is not spectral overlap among the different channels. Image reconstruction, algorithms, and displays are similar to those for single wavelength imaging described herein.

Example 8

Frequency Domain Technology

The TR system described herein can be modified by using one or more frequency domain sources, preferably at multiple frequencies. The theoretical formulation is written in the frequency domain so that the use of frequency technology is directly applied to the existing algorithms. The rationale behind using frequency domain technology is similarly to TR technology in that it yields multi-frequency information that can differentiate absorption and scattering in intrinsic contrast mode and fluorophore concentration and life-time in fluorescence mode. If frequency technology is used, the instrument in FIG. 4A is substituted by sources modulated at one or several frequencies and detection channels that are responsible for signal demodulation, such as lock-in amplifiers or preferably quadrature demodulators, similar to the ones used for the detection of MR signals.

Example 9

Differential Dynamic Imaging (DDI)

The implementation of the composite measurements described above can be applied in several ways to obtain fluorescent and intrinsic contrast, and to construct the AR images. For example, whereas a general scheme of an animal injected with a NIRF molecular probe is considered in Eqs. 4 and 5, one could obtain measurements from an animal before injection of the NIRF probe and then obtain differential measurements of absorption and fluorescent contrast after NIRF probe injection. This technique has important applications in monitoring the kinetics of uptake and activation (as also demonstrated in Example 2). This approach also yields the most accurate results since differential measurements allow for the reconstruction of the fluorochrome/chromophore absorption independently of background absorption (since only the absorption change can be reconstructed). Therefore, more accurate AR maps can be produced as a function of time.

Example 10

Imaging at Multiple Wavelengths

An alternative implementation of composite measurements than the one used in Example 9 is to employ four or more wavelengths for each measurement set. For N tissue chromophores, N or more of these wavelengths are selected at a spectral region where the NIRF probe does not absorb. Therefore, true "intrinsic" contrast is obtained, i.e., contrast that is due only to the natural tissue chromophore concentrations. Using the spectral information of these chromophores, one can calculate their absorption at the emission and excitation wavelengths of the NIRF probe. The other two wavelengths are used to construct absorption images at the excitation and emission wavelengths. Those latter images reconstruct absorption due to both the natural tissue chromophore concentration and the fluorochrome distribution. By subtracting the images obtained at the excitation or emission wavelength from the absorption images calculated only for the tissue natural chromophores, one can obtain the true fluorochrome/chromophore concentration.

Example 11

Clinical FMT System

The new systems and methods described herein are easily applied to a clinical setting. For example breast cancer detection can be achieved with a circular/cylindrical multipoint incident illumination array or with a compression/planar array. Brain measurements can be made with an elastic band of optical fibers attached to the the scull or a planar/reflectance geometry could be applied. See FIGS. 3A-F for various arrays. The described FMT imaging methods can be conducted sequentially or simultaneously with MR or CT measurements, because the optical technology is compatible with other radiological modalities.

In a clinical setting, CW measurements would be useful for the economical collection of large numbers of measurements. However, even a limited number of more advanced technologies (e.g., IM or TR as described above) can significantly improve the information content of the CW measurements. However, it is envisaged that a clinical system can be built entirely based on CW technology. As frequency-domain or time-domain technologies become cheaper, the whole system can be based only on frequency-domain or time-domain technologies.

OTHER EMBODIMENTS

A subcategory of the general reconstruction scheme of molecular activation described herein would be the use of simple transillumination of tissue for the detection of molecular events. This is a relaxation of the tomographic imaging to simple projection imaging, similar, but not same as the one described previously for reflectance imaging (Weissleder et al., U.S. Pat. No. 6,083,486). Transillumination allows for measurements of absorbers of fluorochromes through the whole tissue, therefore it achieves penetration of several centimeters, in contrast to reflectance imaging that can penetrate only for a few centimeters at the most. Transillumination of molecular events cannot three-dimensionally resolve or quantify molecular activity but can still be used to monitor qualitatively relative changes of molecular activation.

In another embodiment, the new systems and methods can be used to image endogenous fluorescence in an animal. For example, a gene encoding a fluorescent protein, such as green fluorescent protein or fluorescein, can be included adjacent to a gene of interest that is to be expressed in an animal or human patient using standard gene therapy techniques. The expression of the gene of interest can be determined indirectly by imaging the fluorescent protein. If this protein is expressed, then the gene of interest has also been expressed.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of imaging a distribution of a near-infrared fluorescent molecular probe within a region of an animal, the method comprising:
   (a) generating a surface representation of the animal;
   (b) sequentially transmitting excitation light into the animal at each of a plurality of locations to transilluminate the region of the animal;
   (c) following illumination at each of the plurality of locations, obtaining an image of fluorescent light emitted from the near-infrared fluorescent molecular probe within the animal; and
   (d) generating a three-dimensional tomographic representation of the probe distribution within the region of the animal using the images obtained in step (c) and using the surface representation,
   wherein the surface representation comprises an identification of positions of an incident illumination array and/or detection array arranged on a substrate that conforms to the animal body, and wherein generating a three-dimensional tomographic representation comprises using the identified positions in an optical reconstruction.

2. A method of imaging a distribution of a near-infrared fluorescent molecular probe within a region of an animal, the method comprising:
   (a) sequentially transmitting excitation light into the animal at each of a plurality of locations to transilluminate the region of the animal;
   (b) following illumination at each of the plurality of locations, obtaining an image of fluorescent light emitted from the near-infrared fluorescent molecular probe within the animal;
   (c) generating a surface representation of the animal, wherein the surface representation comprises an identification of positions of incident illumination and/or detection; and
   (d) generating a three-dimensional tomographic representation of the probe distribution within the region of the animal using the images obtained in step (b) and using the surface representation,
   wherein generating the tomographic representation in step (d) comprises iteratively solving for the fluorescent probe distribution using an excitation light propagation model and an emission light propagation model.

3. The method of claim 2, wherein the excitation light is continuous wave light.

4. The method of claim 2, wherein the excitation light is near-infrared.

5. The method of claim 2, wherein the excitation light wavelength is within a range from about 600 to 1000 nanometers.

6. The method of claim 2, wherein the excitation light wavelength is within a range from about 670 to 850 nanometers.

7. The method of claim 2, further comprising combining the representation of the fluorescent probe distribution with any one or more of magnetic resonance, x-ray computed tomography, ultrasound, single photon emission tomography, or positron emission tomography imaging data.

8. The method of claim 2, wherein the probe comprises a fluorochrome attached to a delivery vehicle, comprising any one or more of a polymer, a dendrimer, a protein, a carbohydrate, a lipid sphere, and a nanoparticle.

9. The method of claim 2, wherein the probe comprises a member selected from the group consisting of an activatable fluorescent probe, a targeted fluorescent probe, a fluorescent protein, quantum dots, an enzyme-activatable fluorescent probe, a receptor-targeted near-infrared fluorochrome, an antibody-targeted near-infrared fluorochrome, a wavelength-shifting beacon, a multi-color fluorescence probe, and a lanthanide metal-ligand probe.

10. The method of claim 2, wherein the probe has at least one of the following properties: the probe becomes activated upon target interaction; the probe becomes deactivated after target interaction; the probe changes its quantum yield upon target interaction; the probe changes its fluorescence lifetime after target interaction; the probe changes its fluorescent spectrum after target interaction; and the probe has high binding affinity to a target.

11. The method of claim 2, wherein the surface representation comprises an identification of positions of a multipoint incident illumination array.

12. The method of claim 11, wherein the multipoint incident illumination array is selected from the group consisting of a planar array, a cylindrical array, a curved array, and an uneven array.

13. The method of claim 12, wherein the multipoint incident illumination array is a planar array.

14. The method of claim 11, wherein the multipoint incident illumination array is part of a catheter-like device.

15. A method of imaging a distribution of a near-infrared fluorescent molecular probe within a region of an animal, the method comprising:
(a) sequentially transmitting excitation light into the animal at each of a plurality of locations to transilluminate the region of the animal;
(b) following illumination at each of the plurality of locations, obtaining an image of fluorescent light emitted from the near-infrared fluorescent molecular probe within the animal;
(c) generating a surface representation of the animal, wherein the surface representation comprises an identification of positions of incident illumination and/or detection; and
(d) generating a three-dimensional tomographic representation of the probe distribution within the region of the animal using the images obtained in step (b) and using the surface representation,
wherein generating the tomographic representation in step (d) comprises using a forward model of an excitation field from the excitation light source to the fluorescent probe within the animal and an emission field from the fluorescent probe within the animal to the detector.

16. A method of imaging a distribution of a near-infrared fluorescent molecular probe within a region of an animal, the method comprising:
(a) sequentially transmitting excitation light into the animal at each of a plurality of locations to transilluminate the region of the animal;
(b) following illumination at each of the plurality of locations, obtaining an image of fluorescent light emitted from the near-infrared fluorescent molecular probe within the animal;
(c) generating a surface representation of the animal, wherein the surface representation comprises an identification of positions of incident illumination and/or detection; and
(d) generating a three-dimensional tomographic representation of the probe distribution within the region of the animal using the images obtained in step (b) and using the surface representation,
wherein generating the tomographic representation in step (d) comprises using a measure of the excitation light.

17. The method of claim 16, wherein the surface representation is generated using one or more of magnetic resonance imaging, ultrasound, or computed tomography imaging.

18. The method of claim 16, wherein the excitation light is continuous wave light.

19. The method of claim 16, wherein the excitation light is near-infrared.

20. The method of claim 16, wherein the excitation light wavelength is within a range from about 600 to 1000 nanometers.

21. The method of claim 16, wherein the excitation light wavelength is within a range from about 670 to 850 nanometers.

22. The method of claim 16, further comprising combining the representation of the fluorescent probe distribution with any one or more of magnetic resonance, x-ray computed tomography, ultrasound, single photon emission tomography, or positron emission tomography imaging data.

23. The method of claim 16, wherein the probe comprises a fluorochrome attached to a delivery vehicle, comprising any one or more of a polymer, a dendrimer, a protein, a carbohydrate, a lipid sphere, and a nanoparticle.

24. The method of claim 16, wherein the probe comprises a member selected from the group consisting of an activatable fluorescent probe, a targeted fluorescent probe, a fluorescent protein, quantum dots, an enzyme-activatable fluorescent probe, a receptor-targeted near-infrared fluorochrome, an antibody-targeted near-infrared fluorochrome, a wavelength-shifting beacon, a multi-color fluorescence probe, and a lanthanide metal-ligand probe.

25. The method of claim 16, wherein the probe has at least one of the following properties: the probe becomes activated upon target interaction; the probe becomes deactivated after target interaction; the probe changes its quantum yield upon target interaction; the probe changes its fluorescence lifetime after target interaction; the probe changes its fluorescent spectrum after target interaction; and the probe has high binding affinity to a target.

26. A method of imaging a distribution of a near-infrared fluorescent molecular probe within a region of an animal, the method comprising:
(a) sequentially transmitting excitation light into the animal at each of a plurality of locations to transilluminate the region of the animal;

(b) following illumination at each of the plurality of locations, obtaining an image of fluorescent light emitted from the near-infrared fluorescent molecular probe within the animal;

(c) generating a surface representation of the animal, wherein the surface representation comprises an identification of positions of incident illumination and/or detection; and (d) generating a three-dimensional tomographic representation of the probe distribution within the region of the animal using the images obtained in step (b) and using the surface representation, wherein generating the tomographic representation in step (d) comprises compensating for autofluorescence of the region of the animal.

27. The method of claim 26, wherein the excitation light is continuous wave light.

28. The method of claim 26, wherein the excitation light is near-infrared.

29. The method of claim 26, wherein the excitation light wavelength is within a range from about 600 to 1000 nanometers.

30. The method of claim 26, wherein the excitation light wavelength is within a range from about 670 to 850 nanometers.

31. The method of claim 26, further comprising combining the representation of the fluorescent probe distribution with any one or more of magnetic resonance, x-ray computed tomography, ultrasound, single photon emission tomography, or positron emission tomography imaging data.

32. The method of claim 26, wherein the probe comprises a fluorochrome attached to a delivery vehicle, comprising any one or more of a polymer, a dendrimer, a protein, a carbohydrate, a lipid sphere, and a nanoparticle.

33. The method of claim 26, wherein the probe comprises a member selected from the group consisting of an activatable fluorescent probe, a targeted fluorescent probe, a fluorescent protein, quantum dots, an enzyme-activatable fluorescent probe, a receptor-targeted near-infrared fluorochrome, an antibody-targeted near-infrared fluorochrome, a wavelength-shifting beacon, a multi-color fluorescence probe, and a lanthanide metal-ligand probe.

34. The method of claim 26, wherein the probe has at least one of the following properties: the probe becomes activated upon target interaction; the probe becomes deactivated after target interaction; the probe changes its quantum yield upon target interaction; the probe changes its fluorescence lifetime after target interaction; the probe changes its fluorescent spectrum after target interaction; and the probe has high binding affinity to a target.

35. A fluorescence molecular tomography imaging system comprising:
an excitation light source;
an optical imaging apparatus configured to sequentially direct light from the excitation light source into an animal at a plurality of locations, to transilluminate a region of the animal;
a detector configured to obtain an image of fluorescent light emitted from a fluorescent probe within the region of the animal following illumination at each of the plurality of locations;
a processor configured to obtain a tomographic representation of a three-dimensional distribution of the fluorescent probe within the region of the animal using the images of fluorescent light emitted from the fluorescent probe; and
a device configured to generate a surface representation of the animal, wherein the processor is configured to determine the three-dimensional distribution of the fluorescent probe using the surface representation and using the images of fluorescent light emitted from the fluorescent probe,
wherein the surface representation comprises a representation of positions of an incident illumination array and/or detection array arranged on a substrate that conforms to the animal body.

36. The system of claim 35, wherein the processor is configured to generate the tomographic representation using the positions of the illumination array and/or detection array in an optical reconstruction.

37. A fluorescence molecular tomography imaging system comprising:
an excitation light source;
an optical imaging apparatus configured to sequentially direct light from the excitation light source into an animal at a plurality of locations, to transilluminate a region of the animal;
a detector configured to obtain an image of fluorescent light emitted from a fluorescent probe within the region of the animal following illumination at each of the plurality of locations;
a device configured to generate a surface representation of the animal, wherein the surface representation comprises a representation of positions of incident illumination and/or detection; and
a processor configured to obtain a tomographic representation of a three-dimensional distribution of the fluorescent probe within the region of the animal using the images of fluorescent light emitted from the fluorescent probe and using the surface representation,
wherein the processor is configured to iteratively solve for the three-dimensional fluorescent probe distribution using an excitation light propagation model and an emission light propagation model.

38. The fluorescence molecular tomography imaging system of claim 37, wherein the surface representation comprises an identification of positions of a multipoint incident illumination array, wherein the multipoint incident illumination array is selected from the group consisting of a planar array, a cylindrical array, a curved array, and an uneven array.

39. The fluorescence molecular tomography imaging system of claim 37, wherein the surface representation comprises an identification of positions of a multipoint incident illumination array, wherein the multipoint incident illumination array is part of a catheter-like device.

40. A fluorescence molecular tomography imaging system comprising:
an excitation light source;
an optical imaging apparatus configured to sequentially direct light from the excitation light source into an animal at a plurality of locations, to transilluminate a region of the animal;
a detector configured to obtain an image of fluorescent light emitted from a fluorescent probe within the region of the animal following illumination at each of the plurality of locations;
a device configured to generate a surface representation of the animal, wherein the surface representation comprises a representation of positions of incident illumination and/or detection; and
a processor configured to obtain a tomographic representation of a three-dimensional distribution of the fluorescent probe within the region of the animal using the images of fluorescent light emitted from the fluorescent probe and using the surface representation, wherein the processor is configured to obtain the tomographic representation using a forward model of an excitation field from the excitation light source to the fluorescent probe within the animal and an emission field from the fluorescent probe within the animal to the detector.

41. A fluorescence molecular tomography imaging system comprising:

an excitation light source;

an optical imaging apparatus configured to sequentially direct light from the excitation light source into an animal at a plurality of locations, to transilluminate a region of the animal;

a detector configured to obtain an image of fluorescent light emitted from a fluorescent probe within the region of the animal following illumination at each of the plurality of locations;

a device configured to generate a surface representation of the animal, wherein the surface representation comprises a representation of positions of incident illumination and/or detection; and a processor configured to obtain a tomographic representation of a three-dimensional distribution of the fluorescent probe within the region of the animal using the images of fluorescent light emitted from the fluorescent probe and using the surface representation, wherein the processor is configured to obtain the tomographic representation using a measure of the excitation light.

42. The system of claim 41, wherein the device configured to generate a surface representation of the animal comprises one or more of a magnetic resonance imaging device, an ultrasound device, and a computed tomography imaging device.

43. The system of claim 41, wherein the excitation light source provides near-infrared light.

44. The system of claim 41, wherein the excitation light source provides light of a wavelength within a range from about 600 to 1000 nanometers.

45. The system of claim 41, wherein the excitation light source provides light of a wavelength within a range from about 670 to 850 nanometers.

46. The system of claim 41, wherein the processor is configured to combine the tomographic representation of the three-dimensional distribution of the fluorescent probe with an anatomical image obtained from a magnetic resonance, x-ray computed tomography, ultrasound, single photon emission tomography, or positron emission tomography system.

47. The system of claim 41, further comprising a display configured to display the tomographic representation.

48. A fluorescence molecular tomography imaging system comprising:

an excitation light source;

an optical imaging apparatus configured to sequentially direct light from the excitation light source into an animal at a plurality of locations, to transilluminate a region of the animal;

a detector configured to obtain an image of fluorescent light emitted from a fluorescent probe within the region of the animal following illumination at each of the plurality of locations;

a device configured to generate a surface representation of the animal, wherein the surface representation comprises a representation of positions of incident illumination and/or detection; and a processor configured to obtain a tomographic representation of a three-dimensional distribution of the fluorescent probe within the region of the animal using the images of fluorescent light emitted from the fluorescent probe and using the surface representation, wherein the processor is configured to compensate for autofluorescence of the region of the animal in obtaining the tomographic representation.

* * * * *